US006417150B2

(12) United States Patent
Willey

(10) Patent No.: US 6,417,150 B2
(45) Date of Patent: *Jul. 9, 2002

(54) LOW HUE PHOTOBLEACHES

(75) Inventor: Alan David Willey, Cincinnati, OH (US)

(73) Assignee: Case Western Reserve University, Cleveland, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/355,154
(22) PCT Filed: Jan. 22, 1998
(86) PCT No.: PCT/US98/00225
§ 371 (c)(1),
(2), (4) Date: Jul. 23, 1999
(87) PCT Pub. No.: WO98/32832
PCT Pub. Date: Jul. 30, 1998

Related U.S. Application Data
(60) Provisional application No. 60/035,903, filed on Jan. 24, 1997.

(51) Int. Cl.$^7$ ................................................. C11D 7/22
(52) U.S. Cl. ....................................................... 510/301
(58) Field of Search ................................. 510/301, 367

(56) References Cited

U.S. PATENT DOCUMENTS

| | | | | |
|---|---|---|---|---|
| 3,094,536 A | 6/1963 | Kenney et al. | ........... | 260/314.5 |
| 3,927,967 A | 12/1975 | Speakman | ...................... | 8/103 |
| 4,033,718 A | 7/1977 | Holcombe et al. | .............. | 8/103 |
| 4,166,718 A | 9/1979 | Reinert et al. | ................... | 8/111 |
| 4,240,920 A | 12/1980 | de Luque | ..................... | 252/99 |
| 4,255,273 A | 3/1981 | Sakkab | ........................ | 252/102 |
| 4,256,597 A | 3/1981 | Sakkab | ........................ | 252/99 |
| 4,318,883 A | 3/1982 | Polony et al. | ................. | 422/22 |
| 4,368,053 A | 1/1983 | Eckhardt et al. | ............... | 8/102 |
| 4,497,741 A | 2/1985 | Hölzle et al. | .......... | 260/245.77 |
| 4,648,992 A | 3/1987 | Graf et al. | ................... | 540/124 |
| 5,916,481 A | * 6/1999 | Willey | ................... | 252/186.21 |

FOREIGN PATENT DOCUMENTS

| | | | | |
|---|---|---|---|---|
| EP | 0 285965 | 10/1988 | ........... | C09B/67/22 |
| EP | 0 381211 | 8/1990 | ............ | G11B/7/24 |
| EP | 0 484027 | 5/1992 | ........... | C09B/47/04 |
| GB | 1372035 | 10/1974 | | |
| GB | 1408144 | 1/1975 | | |
| GB | 2159516 | 12/1985 | ........... | C09B/47/04 |
| JP | 6-73397 | 3/1994 | ........... | C11D/3/395 |
| WO | WO 91/18006 | 11/1991 | ............ | C07J/43/00 |

OTHER PUBLICATIONS

Brasseur, N., et al., "Synthesis and Photodynamic Activities of Silicon 2,3–Naphthalocyanine Derivatives", J. Med. Chem., vol. 37, p. 415–420 (1994).
Chan, W.S., et al., "Photosensitising Activity of Phthalocyanine Dyes Screened Against Tissue Culture Cells", Angew Photochemistry & Photobiology, vol. 45, No. 6, pp. 757–761 (1987).
Cook, M.J. et al., "Octa–alkoxy Phthalocyanine and Naphthalocyanine Dertivatives: Dyes with Q–band Absorption in the Far Red or Near Infrared" J. Chem. Soc., Perkin Trans., vol. I., p. 2453–2458 (1988).
Dirk, C.W., et al., "Cofacial Assembly of Partially Oxidized Metallomacrocycles as an Approach to Controlling Lattice Architecture in Low–Dimensional Molecular Solids. Chemical and Architectural Properties of the "Face–toFace" Polymers [M(phthalocyaninato)O] Where M= Si, Ge, and Sn", J. Am. Chem. Soc., vol. 105, pp. 1539–1550 (1983).
Esposito, J.N. et al., "The Synthesis and Physical Properties of Some Organo– and Organosiloxysilicon Phthalocyanines", Inorg. Chem., vol. 5, No. 11, pp. 1979–1984 (Nov. 1966).
Ford, W.E. et al., "Synthesis and Photochemical Properties of Aluminum, Gallium, Silicon, an Tin Naphthalocyanines", Inorg. Chem., vol. 31, p. 3371–3377 (1992).
Hayashida, S., et al., "Effect of Axial Substituents on the Aggregate of Silicon Naphthalocyanine in the Vacuum Deposited Thin Films", Chem. Lett., pp. 2137–2140 (1990).
Joyner, R.D. et al, "Phthalocyaninosilicon Compounds", Inorg. Chem., vol. 1, No. 2, pp. 236–238 (May 1962).
Kato, S., et al., "Preparation of a New Series of Trinuclear Metallophthalocyanines and –porphyrins", Angew. Chem. Int. Ed. Engl., vol. 18, No. 1, pp. 82–83 (a979).
Kraut, B., et al., "Photochemical Properties of Tin(IV) Phthalocyanines: a Comparison between the Dichloro and Superphthalocyanines", Inorganica Chimica Acta, vol. 149, pp. 273–277 (1988).
Kroenke, W.E. et al., "A Series of Phthalocyaninotin Complexes", Inorg. Chem., vol. 3, No. 2, pp. 251–254 (Feb. 1964).

(List continued on next page.)

Primary Examiner—John Hardee
(74) Attorney, Agent, or Firm—Fay, Sharpe, Fagan, Minnich & McKee, LLP

(57) ABSTRACT

Low hue photobleaching compositions comprising organotin (IV), organogermanium (IV), organoplatinum (IV), organopalladium (IV), organolead (IV) or organophosphorous (III) phthalocyanine and naphthalocyanines having Q-band absorption maxima at wavelengths greater than 660 nm and increased triplet state yields whereby production of singlet oxygen is increased. Use of $Sn^{4+}$, $Ge^{4+}$, $Pt^{4+}$, $Pd^{4+}$, $Pb^{4+}$, $P^{3+}$ phthalocyanine and naphthalocyanines compounds in photobleaching compositions allows for formulation of low hue laundry compositions, bleach compositions, and hard surface cleaners.

20 Claims, No Drawings

Kroenke, W.E. et al., "The Infrared Spectra of Some Tin and Lead Phthalocyanines", Inorg. Chem., vol. 3, No. 5, pp. 696–698 (May 1964).

Lowery, M.H. et al., "Dichloro(phthalocyanino)silicon", Inorg. Chem., vol. 4, p. 128 (1965).

Moyer, T. J., et al., "Iodine Doped $(SiNcO)_n$—A new Conducting Polymer", Polymer Preps, vol. 25, p. 234–235 (1986).

Nyokong, T., "Photoreduction of Tin(IV) Phthalocyanines", Polyhedron, vol. 13, No. 13, pp. 2067–2071 (1994).

Rafaeloff, R., et al., "New Group IV Phthalocyanines", J. Inorg. Nucl. Chem., vol. 28, pp. 899–902 (1966).

Rihter, B.D., "Synthesis and Photoproperties of Diamagnetic Octabutoxyphthalocyanines with Deep Red Optical Absorbance", J. Am. Chem. Soc., vol. 112, pp. 8064–8070 (1990).

Sayer, P., "Metalloid Porphyrins and Phthalocyanines", Acc. Chem. Res., vol. 15, pp. 73–79 (1982).

Snow, A. W., "Molecular Associattion and Monolayer Formation of Soluble Phthalocyanine Compounds", J. Am. Chem. Soc., vol. 106, pp. 4706–4711 (1984).

Soncin, M., et al., "Effect of the Delivery System on the Biodistribution of Ge(IV) octabutoxy–phthalocyanines in Tumour–bearing Mice", Cancer Letters, vol. 89, pp. 101–106 (1995).

Wen, T–C., et al., "Synthesis and Photoproperties of Silicon Phthalocyanines and Silicon Naphthalocyanines", J. Chin. Chem. Soc., vol. 40, pp. 141–147 (1993).

Wheeler, B.L. et al., "A Silicon Phthalocyanine and a Silicon Naphthalocyanine; Synthesis, Electrochemistry, and Electrogenerated Chemiluminescence", J. Am. Chem. Soc., vol. 106, p. 7404–7410 (1984).

Witkiewic, Z. et al., "Properties of Octamethoxyphthalocyanines I. On their syntheses, electrical conductivity, and catalytic activity", Material Science, vol. 11, No. 1–2, pp. 39–45 (1976).

* cited by examiner

LOW HUE PHOTOBLEACHES

This claims priority to U.S. Provisional Application 60/035,903, filed Jan. 24, 1997.

FIELD OF THE INVENTION

The present invention relates to novel organotin, organogermanium, organoplatinum, organopalladium, organolead, or organophosphorous photosensitizing compounds having a Q-band maximum absorption wavelength of 660 nanometers or greater and their use as photoactivators (photosensitizer) or singlet oxygen producers, in particular for low hue photobleaching for removing stains from textiles and hard surfaces. The present invention also relates to laundry compositions and hard surface cleaners comprising the novel organotin, organogermanium, organoplatinum, organopalladium, organolead, or organophosphorous photosensitizing compounds of the present invention. The present invention further relates to a method of delivering compositions comprising low hue photobleaches to soiled and stained fabrics and to hard surfaces.

BACKGROUND OF THE INVENTION

It is known that certain water-soluble phthalocyanine, naphthalocyanine, and metallocyanine compounds can be used as photobleaching and anti-microbial agents. Phthalocyanines and naphthalocyanines or their metal complexes can form "singlet oxygen" an oxidative species capable of reacting with stains to bleach them to a colorless and usually water-soluble state.

There are many examples of phthalocyanines and naphthalocyanines photobleaches, the most common being the zinc and aluminum phthalocyanines. In the literature the term "photosensitizer" is often used instead of "photoactivator" and may therefore be considered as standing equally well for the latter term used throughout this specification The prior art teaches phthalocyanine and naphthalocyanine compounds having the general structure

where Me is a transition or non-transition metal, (Sens.) is a phthalocyanine or naphthalocyanine ring which, when combined with a suitable Me unit, is capable of undergoing photosensitization of oxygen molecules, R units are substituent groups which are bonded to the photosensitization ring units (Sens.) to enhance the solubility or photochemical properties of the molecule, and Y units are substituents associated with the metal atom, for example, anions to provide electronic neutrality. The selection of a particular substituent R unit for substitution into the molecule has been the focus of many years of research and these units are typically chosen by the formulator to impart into the target molecule the desired level of water solubility.

A major limitation to the use of phthalocyanine and naphthalocyanine compounds for fabric photobleaching is the fact that these molecules are highly colored materials.

A second limitation is that the compounds are not inherently water soluble. It has therefore been the task of phthalocyanine and naphthalocyanine photobleach formulators to provide water soluble photobleaches without adversely affecting their photochemical properties.

A further task for the formulators of photobleaches has been the need to modify the properties of the photosensitizer (Sens.) unit of the molecule, in other words, to increase the quantum efficiency without reducing the water solubility. While balancing water solubility and enhanced photophysics. the formulator must insure that the structural modifications do not increase the color.

It is well known to formulators skilled in the art that an R unit which may produce a desired increase in one of these three properties may cause an equally large decrease in one or both of the other desirable properties.

Surprisingly, it has been found that the compounds of the present invention allow the formulators to modify the levels of solubility, photoefficiency, Q-band wavelength maxima separately without adversely affecting the other parameters of the molecule. This ability to delineate and selectively modify the key structural elements contributing to the target properties of the molecule allows the formulator to proceed without having to rely upon a "hit and miss" stratagem.

The photobleaches of the invention comprise two "elements". The photosensitizing ring which is optimized for color (hue) and generation of singlet oxygen, and axial groups which are optimized to provide the desired level of solubility, substantivity, and de-aggregation. These two elements will be described in more detail herein below.

One key to this ability to control the molecular properties is found when contrasting the structure of known photobleaches comprising phthalocyanines and naphthalocyanines with those of the present invention. The examples of photo-bleaches previously described in the art are generally flat molecules due to their planar ring structure. This planarity produces an propensity for these molecules to aggregate wherein this aggregation tends to lead to photochemical quenching, preventing efficient formation of singlet oxygen.

The organotin, organogermanium, organoplatinum, organopalladium, organolead, or organophosphorous photosensitizing compounds of the present invention comprise axial substituents that act to break up this ordering effect, hence providing an efficiently formed mono-layer of photosensitizers evenly applied to a given substrate. Because each molecule of this mono-layer can now contribute to bleaching there is better cost efficiency to the formulator.

It has been surprisingly found that because of the separating out of physical properties into "molecular sectors", e.g. R groups for solubility, new uses for the compounds of the present invention have been realized. Adducts which provide unique solubility profiles, but which detract from the photophysics, were once excluded from use in photobleaches. However, the inclusion of these moieties into the photobleaches of the present invention results in the ability to formulate photobleaches for use in non-classical applications, for example dry cleaning applications. Solvent based or low aqueous solutions of the present invention are now obtainable for the very reason that the present invention provides control over solubility which is manifested in the choice of the axial R substitutions.

The proper selection of axial R units attached to the compounds of the present invention allow the formulator to balance the changes in photoefficiency of the desired compound with the water solubility of the parent material. In addition, these axial R unit modifications provide the formulator with the ability to balance solubility, Q-band $\lambda_{max}$, and quantum efficiency of the (Sens.) unit.

It is an object of the present invention to provide "substantive" and "non-substantive" organotin, organogermanium, organoplatinum, organopalladium, organolead, or organophosphorous photosensitizers. A "substantive" organotin, organogermanium, organoplatinum, organopalladium, organolead, or organophosphorous photosensitizer will be attracted to a surface and a "non-substantive" organotin, organogermanium, organoplatinum, organopalladium, organolead, or organophosphorous photosensitizer will repel a surface.

It is a further object of the present invention to provide substantive and non-substantive photobleaching laundry compositions for natural, synthetic or blended fabrics.

It is a further object of the present invention to provide photobleaching compositions that comprise non-aqueous and low aqueous carriers, that is, photobleaching compositions having carriers wherein water constitutes less than half of the carrier liquid.

It is a further object of the present invention to provide substantive and non-substantive photobleaching hard surface cleaning compositions for non-porous hard surfaces, inter alia, Formica®, ceramic tile, glass, or for porous hard surfaces such as concrete or wood.

An object of the present invention is to provide a method for bleaching fabric with laundry compositions comprising organotin, organogermanium, organoplatinum, organopalladium, organolead, or organophosphorous photobleaching compounds of the present invention.

An object of the present invention is to provide a method for cleaning hard surfaces with compositions comprising organotin, organogermanium, organoplatinum, organopalladium, organolead, or organophosphorous photobleaching compounds of the present invention.

An object of the present invention is to provide for low hue organotin, organogermanium, organoplatinum, organopalladium, organolead, or organophosphorous photosensitizing compounds having a Q-band maximum absorption wavelength of at least 660 nanometers.

BACKGROUND ART

Various patent documents relate to photochemical bleaching or to the use of phthalocyanine and naphthalocyanine compounds as well as their formulation and synthesis. See for example U.S. Pat. No. 3,094,536 issued Jun. 18, 1963; U.S. Pat. No. 3,927,967 issued Dec. 23, 1975; U.S. Pat. No. 4,033,718 issued Jul. 5, 1977; U.S. Pat. No. 4,166,718 issued Sep. 4, 1979; U.S. Pat. No. 4,240,920 issued Dec. 23, 1980; U.S. Pat. No. 4,255,273 issued Mar. 10, 1981; U.S. Pat. No. 4,256,597 issued Mar. 17, 1981; U.S. Pat. No. 4,318,883 issued Mar. 9, 1982; U.S. Pat. No. 4,368,053 issued Jan. 11, 1983; U.S. Pat. No. 4,497,741 issued Feb. 5, 1985; U.S. Pat. No. 4,648,992 issued Mar. 10, 1987; and U.K. Pat. App. 1,372,035 published Oct. 30, 1974; U.K Pat. App. 1,408,144 published Oct. 1, 1975; U.K. Pat App. 2,159,516 published Dec. 4, 1985; E.P. 484,027 A1 published May 6, 1992; WO 91/18006 published Nov. 28, 1991 and Japanese Kokai 06-73397 Derwent Abst. No. (94-128933) published Mar. 15, 1994.

In addition to the above cited patent publications, other references describing the synthesis, preparation and properties of phthalocyanines and naphthalocyanines, incorporated herein also by reference; *Phthalocyanines: Properties and Applications*, Leznoff, C. C. and Lever A. B. P. (Eds), VCH, 1989; *Infrared Absorbing Dyes*, Matsuoka, M. (Ed), Plenum, 1990; *Inorg. Chem., Lowery*, M. J. et al., 4, pg. 128, (1965); *Inorg. Chem.* Joyner R. D. et al., 1, pg. 236, (1962); *Inorg. Chem.*, Kroenke, W. E. et al., 3, 696, 1964; *Inorg. Chem.* Esposito, J. N. et al., 5, pg. 1979, (1966); *J. Am. Chem. Soc.* Wheeler, B. L. et al., 106, pg. 7404, (1984); *Inorg. Chem.* Ford, W. E, et al., 31, pg. 3371, (1992); *Material Science*, Witkiewicz, Z. et al., 11, pg. 39, (1978); *J. Chem. Soc.* Perkin Trans. I, Cook, M. J., et al., pg. 2453, (1988); *Acc. Chem. Res.*, Sayer, P., Gouterman, M., and Connell, C. R., 15, 73–79, (1982); *J. Am. Chem. Soc.*, Snow, A. W. and Jarvis, N. Lynn, 106, 4706–4711, (1986); *J. Am. Chem. Soc.*, Richter, B. D., Kenney, M. E., Ford, W. E. and Rodgers, M. A. J., 112, 8064–8070, (1990); *Cancer Letters*, Soncin M., Polo, L., Reddi, E., Jori, G., Kenny, M. E., Chang, G., and Rodgers, M. A. J., 89, 101–106, (1995); *J. Inorg, Nucl. Chem.*, Rafaeloff, R., Kohl, F. J., Krueger, P. C., Kenney, M. E., 28, 899–902, (1966); *J. Amer. Chem. Soc.*, Dirk, C. W., Inabe, T., Schoch, Jr., K. F., and Marks, T. J., 105, 1539–1550, (1985); *Polyhedron*, Nyaokong, T., 2067–71, (1994); *Angew. Chem.*, Int. Ed. Engl., Kato, S., Noda, I., Mizuta, M. M., and Itoh, Y., 18, 82–3, (1979); Photochemistry and Photobiology, Chan, W.-S., Marshall, J. F., Svensen, R., Phillips, D., and Hart, I. R., 45, 757–61, (1987); *Inorganica Chemica Acta*, Kraut, B., and Ferrandi, G., 149, 273–77, (1988); *Inorg. Chem.*, Kroenke, W. J., and Kenney, M. E., 3, 251–4, (1964).

SUMMARY OF THE INVENTION

The present invention relates to a photochemical singlet oxygen generator having a Q-band maximum absorption wavelength of 660 nanometers or greater, having the formula:

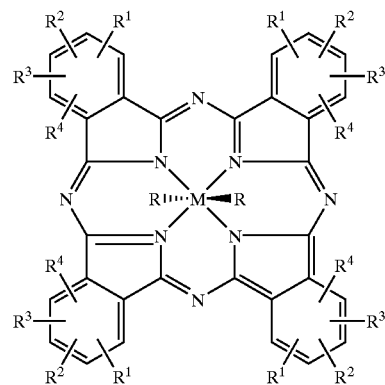

or the formula:

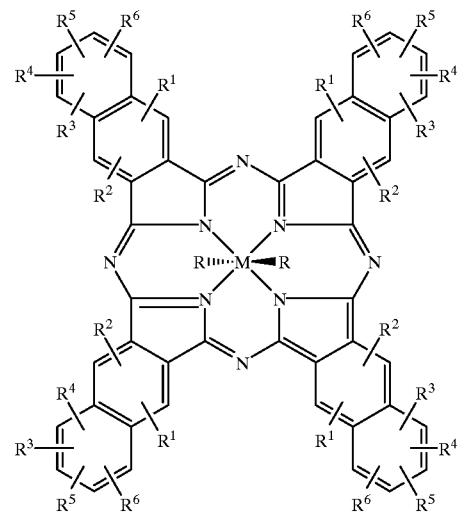

wherein M is a photoactive metal or non-metal, said metal or non-metal selected from the group consisting of Sn, Ge, Pt, Pd, Pb, P and mixtures thereof; $R^1$, $R^2$, $R^3$, $R^4$, $R^5$, and $R^6$ units are each independently selected from the group consisting of:

a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;
h) branched alkoxy having the formula:

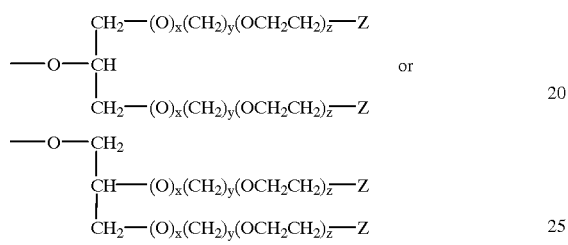

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2+}M$, or mixtures thereof; M is a water soluble cation in sufficient amount to satisfy charge balance; x is 0 or 1, each y independently has the value from 0 to 6, each z independently has the value from 0 to 100;

i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) an ester of the formula —$CO_2R^9$ wherein $R^9$ is
  i) $C_1$–$C_{22}$ alkyl, $C_3$–$C_{22}$ branched alkyl, $C_2$–$C_{22}$ alkenyl, $C_3$–$C_{22}$ branched alkenyl or mixtures thereof;
  ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  iii) polyhydroxyl substituted $C_3$–$C_{22}$ alkylene;
  iv) $C_3$–$C_{22}$ glycol;
  v) $C_1$–$C_{22}$ alkoxy;
  vi) $C_3$–$C_{22}$ branched alkoxy;
  vii) substituted aryl, unsubstituted aryl, or mixtures thereof;
  viii) substituted alkylenearyl, unsubstituted alkylenearyl, or mixtures thereof;
  ix) substituted aryloxy, unsubstituted aryloxy, or mixtures thereof;
  x) substituted oxyalkylenearyl, unsubstituted oxyalkylenearyl, or mixtures thereof;
  xi) substituted alkyleneoxyaryl, unsubstituted alkyleneoxyaryl, or mixtures thereof;

p) an alkyleneamino unit of the formula:

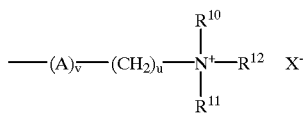

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof; $R^{12}$ is:
  i) hydrogen;
  ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

A is nitrogen or oxygen; X is chlorine, bromine, iodine, or other water soluble anion, v is 0 or 1, u is from 0 to 22;

q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) an alkylethyleneoxy unit of the formula:

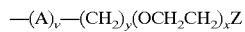

wherein Z is:
  i) hydrogen;
  ii) hydroxyl;
  iii) —$CO_2H$;
  iv) —$SO_3^-M^+$;
  v) —$OSO_3^-M^+$;
  vi) $C_1$–$C_6$ alkoxy;
  vii) substituted aryl, unsubstituted aryl, or mixtures thereof;
  viii) substituted aryloxy, unsubstituted aryloxy, or mixtures thereof;
  ix) alkyleneamino; or mixtures thereof;

A is nitrogen or oxygen, M is a water soluble cation, v is 0 or 1, x is from 0 to 100, y is from 0 to 12;

s) substituted siloxy of the formula:

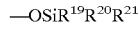

wherein each $R^{19}$, $R^{20}$, and $R^{21}$ is independently
  i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  ii) substituted aryl, unsubstituted aryl, or mixtures thereof;
  iii) substituted aryloxy, unsubstituted aryloxy, or mixtures thereof;
  iv) an alkylethyleneoxy unit of the formula:

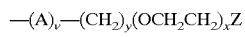

wherein Z is:
  a) hydrogen;
  b) hydroxyl;
  c) —$CO_2H$;
  d) —$SO_3^-M^+$;
  e) —$OSO_3^-M^+$;
  f) $C_1$–$C_6$ alkoxy;
  g) substituted aryl, unsubstituted aryl, or mixtures thereof;

h) substituted aryloxy, unsubstituted aryloxy, or mixtures thereof;
i) alkyleneamino; or mixtures thereof;

A is nitrogen or oxygen, M is a water soluble cation, v is 0 or 1, x is from 0 to 100, y is from 0 to 12;

and mixtures thereof axial R units wherein each R is independently selected from the group consisting of:

a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_2$2 alkoxy;
h) branched alkoxy having the formula:

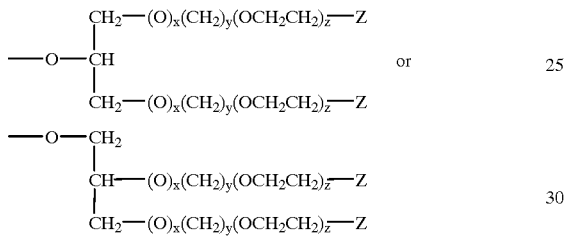

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;
i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
j) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) a carboxylate of the formula:

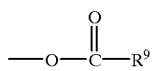

wherein $R^9$ is:
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

iii) polyhydroxyl substituted $C_3$–$C_{22}$ alkylene;
iv) $C_3$–$C_{22}$ glycol;
v) $C_1$–$C_{22}$ alkoxy;
vi) $C_3$–$C_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;
x) substituted oxyalkylenearyl, unsubstituted oxyalkylenearyl, or mixtures thereof;
xi) substituted alkyleneoxyaryl, unsubstituted alkyleneoxyaryl, or mixtures thereof;

p) an alkyleneamino unit of the formula:

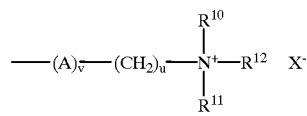

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
$R^{12}$ is:
i) hydrogen;
ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

A is nitrogen or oxygen; X is chlorine, bromine, iodine, or other water soluble anion, v is 0 or 1, u is from 0 to 22;

q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
r) an alkylethyleneoxy unit of the formula:

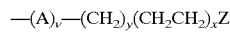

wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;

A is nitrogen or oxygen, M is a water soluble cation, v is 0 or 1, x is from 0 to 100, y is from 0 to 12;

s) substituted siloxy of the formula:

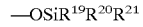

wherein each $R^{19}$, $R^{20}$, and $R^{21}$ is independently i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

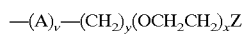

wherein Z is:
a) hydrogen;
b) hydroxyl;
c) —$CO_2H$;
d) —$SO_3^-M^+$;
e) —$OSO_3^-M^+$;
f) $C_1$–$C_6$ alkoxy;
g) substituted aryl, unsubstituted aryl, or mixtures thereof;
h) substituted aryloxy, unsubstituted aryloxy, or mixtures thereof;
i) alkyleneamino, or mixtures thereof;
A is nitrogen or oxygen, M is a water soluble cation, v is 0 or 1, x is from 0 to 100, y is from 0 to 12;
and mixtures thereof.

All percentages, ratios and proportions herein are by weight, unless otherwise specified. All temperatures are in degrees Celsius (° C.) unless otherwise specified. All documents cited are, in relevant part, incorporated herein by reference.

DETAILED DESCRIPTION OF THE INVENTION

The present invention relates to photobleaching compounds and photobleaching compositions. The photobleaching compounds have a Q-band maximum absorption wavelength of 660 nanometers or greater. The photobleaching and photodisinfectants of the present invention are phthalocyanines having the formula:

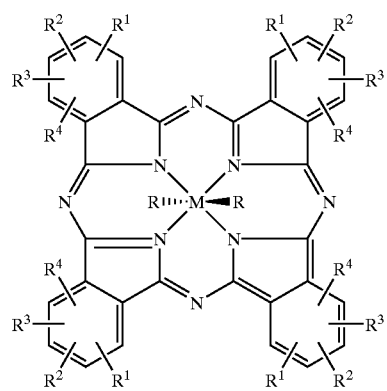

or naphthalocycanines having the formula:

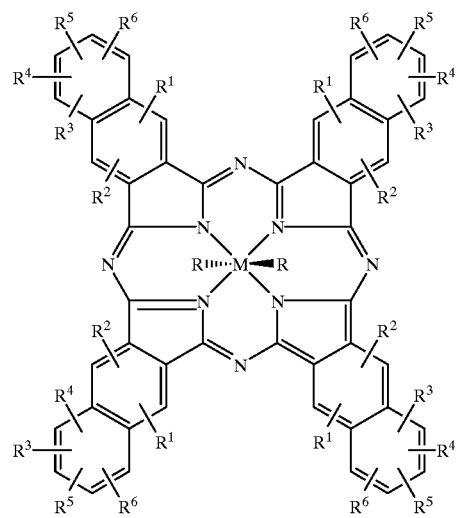

wherein M is a photoactive metal or non-metal, said metal or non-metal selected from the group consisting of Sn, Ge, Pt, Pd, Pb, P, and mixtures thereof. The phthalocyanine and naphthalocyanine rings which comprise the photo sensitizers of the present invention, can be substituted with hydrogen or other units described further herein below. Surprisingly, selection of a suitable $R^1$, $R^2$, $R^3$, $R^4$, $R^5$, or $R^6$ substituent is capable of providing the photobleach or photodisinfectant with a positive $\Delta_{triplet}$ yield of at least 1, preferably at least 10, more preferably at least 30, when said moiety replaces a hydrogen atom. In addition, the selection of a suitable moiety for a $R^1$, $R^2$, $R^3$, $R^4$, $R^5$, or $R^6$ substituent is also capable of providing a positive red shift value of at least 1, preferably a positive red shift value of at least 10, more preferably a positive red shift value of at least 30, when said moieties are substituted for hydrogen.

Each $R^1$, $R^2$, $R^3$, $R^4$, $R^5$, and $R^6$ unit is independently:
a) hydrogen;
b) halogen;
c) hydroxyl;
d) $C_1$–$C_{22}$ alkyl, $C_3$–$C_{22}$ branched alkyl, $C_2$–$C_{22}$ alkenyl, $C_3$–$C_{22}$ branched alkenyl;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl;
f) polyhydroxyl substituted $C_3$–$C_{22}$ alkyl;
g) $C_1$–$C_{22}$ alkoxy, preferably $C_1$–$C_4$ alkoxy, more preferred methoxy;
h) branched alkoxy having the formula

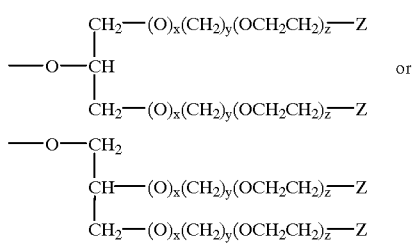

wherein Z is hydrogen, hydroxyl, $C_1$–$C_{30}$ linear alkyl, $C_1$–$C_{30}$ branched alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, preferably from 0 to 6; each z independently has the value from 0 to 100, preferably from 0 to about 10, more preferably from 0 to about 3;

i) substituted aryl, and unsubstituted aryl having the formula:

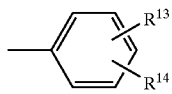

wherein $R^{13}$ and $R^{14}$ are independently selected from the group consisting of hydrogen, $C_1$–$C_6$ alkyl, $C_3$–$C_6$ alkenyl, $C_1$–$C_6$ alkoxy, $C_3$–$C_6$ branched alkoxy, halogen, —$CO_2^-M^+$, —$SO_3^-M^+$, —$OSO_3^-M^+$, —$N(R^{15})_2$, and —$N^+(R^{15})_3X^-$ wherein each $R^{15}$ is independently hydrogen or $C_1$–$C_4$ alkyl; and mixtures thereof; preferably hydrogen $C_1$–$C_6$ alkyl, —$CO_2^-M^+$, —$SO_3^-M^+$, —$OSO_3^-M^+$, and mixtures thereof, more preferably $R^{13}$ or $R^{14}$ is hydrogen and the other moiety is $C_1$–$C_6$ alkyl; wherein M is a water soluble cation and X is a water soluble anion.

j) substituted alkylenearyl and unsubstituted alkylenearyl having the formula:

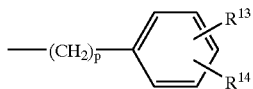

wherein $R^{13}$ and $R^{14}$ are as defined above, p is from 1 to about 10.

k) substituted aryloxy and unsubstituted aryloxy having the formula:

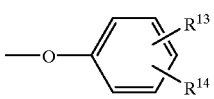

wherein $R^{13}$ and $R^{14}$ are as defined above.

l) substituted alkyleneoxyaryl and unsubstituted alkyleneoxyaryl units are defined as moieties having the formula:

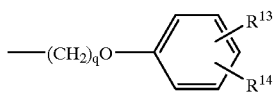

wherein $R^{13}$ and $R^{14}$ are as defined above, q is from 0 to about 10.

m) substituted oxyalkylenearyl and unsubstituted oxyalkylenearyl having the formula:

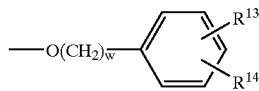

wherein $R^{13}$ and $R^{14}$ are as defined above, w is from about 1 to about 10.

n) $C_1$–$C_{22}$ linear, $C_3$–$C_{22}$ branched thioalkyl, $C_1$–$C_{22}$ linear, $C_3$–$C_{22}$ branched substituted thioalkyl, and mixtures thereof;

o) ester units of the formula —$CO_2R^9$ wherein $R^9$ is $C_1$–$C_{22}$ alkyl, $C_3$–$C_{22}$ branched alkyl, $C_2$–$C_{22}$ alkenyl, $C_3$–$C_{22}$ branched alkenyl, all of which can be substituted with halogen; poly-hydroxyl substituted $C_3$–$C_{22}$ alkyl, $C_3$–$C_{22}$ glycol; $C_1$–$C_{22}$ alkoxy, $C_3$–$C_{22}$ branched alkoxy; substituted and unsubstituted aryl, alkylenearyl, aryloxy, oxyalkylenearyl, alkyleneoxyaryl; preferably $C_1$–$C_{22}$ alkyl, $C_3$–$C_{22}$ branched alkyl, and mixtures thereof;

p) alkyleneamino units having the formula:

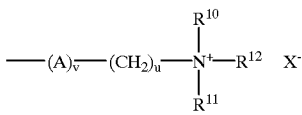

wherein $R^{10}$, and $R^{11}$ are each a $C_1$–$C_{22}$ alkyl, $C_3$–$C_{22}$ branched alkyl, $C_2$–$C_{22}$ alkenyl, $C_3$–$C_{22}$ branched alkenyl, $R^{12}$ is hydrogen, $C_1$–$C_{22}$ alkyl, $C_3$–$C_{22}$ branched alkyl, $C_2$–$C_{22}$ alkenyl, $C_3$–$C_{22}$ branched alkenyl and mixtures thereof, the index v is 0 or 1; X is a other water soluble anion, u is from 0 to 22, preferably u is from 3 to about 10. Examples of water soluble anions include organic species such as fumarate, tartrate, oxalate and the like, inorganic species include chloride, bromide, sulfate, hydrogen sulfate, phosphate and the like;

q) an amino unit of the formula

wherein $R^{17}$ and $R^{18}$ are each a $C_1$–$C_{22}$ alkyl, $C_3$–$C_{22}$ branched alkyl $C_2$–$C_{22}$ alkenyl, $C_3$–$C_{22}$ branched alkenyl, or mixtures thereof;

r) alkylethyleneoxy units having the formula:

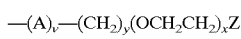

wherein Z is hydrogen, hydroxyl, —$CO_2H$, —$SO_3^-M^+$, —$OSO_3^-M^+$, $C_1$–$C_6$ alkoxy, substituted and unsubstituted aryl, substituted and unsubstituted aryloxy; alkyleneamino as defined herein above; or mixtures thereof; A units comprise nitrogen or oxygen, preferably oxygen; M is a water soluble cation; v is 0 or 1; x is from 0 to 100, preferably from 0 to 20, more preferably from 0 to 5; y is from 0 to 12, preferably from 1 to 4; however, no peroxide —O—O— bonds are contained within the photobleaching compounds of the present invention;

s) siloxy and substituted siloxy of the formula —$OSiR^{19}R^{20}R^{21}$ wherein each $R^{19}$, $R^{20}$, and $R^{21}$ is independently selected from the group consisting of $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof, substituted or unsubstituted aryl, aryloxy; alkyletheneoxy units of the formula:

$$—(A)_v—(CH_2)_y(OCH_2CH_2)_xZ$$

wherein Z is hydrogen, hydroxyl, $C_1$–$C_{30}$ alkyl, —$CO_2H$, —$SO_3^-M^+$, —$OSO_3^-M^+$, $C_1$–$C_6$ alkoxy; substituted or unsubstituted aryl, and aryloxy; alkyleneamino as defined herein above, and mixtures thereof, preferably hydrogen or $C_1$–$C_6$ alkyl, more preferably methyl; v is 0 or 1; x is from 1 to 100, preferably from 0 to about 20, more preferably from 3 to about 10; and y is from 0 to 12, preferably from about 0 to about 5.

Preferred $R^1$, $R^2$, $R^3$, $R^4$, $R^5$, and $R^6$ units are $C_1$–$C_{22}$ alkoxy and halogen, more preferred $R^1$, $R^2$, $R^3$, $R^4$, $R^5$, and $R^6$ units are $C_1$–$C_4$ alkoxy and halogen. When the (Sens.) unit is phthalocyanine most preferred $R^1$, $R^2$, $R^3$, and $R^4$ units are methoxy. When the (Sens.) unit is naphthalocyanine most preferred $R^1$, $R^2$, $R^3$, $R^4$, $R^5$, and $R^6$ units are chlorine, bromine or iodine.

The compounds useful for the present invention also comprise axial R units, wherein R is independently selected from the group consisting of:

a) hydrogen;
b) halogen;
c) hydroxyl;
d) $C_1$–$C_{22}$ alkyl, $C_3$–$C_{22}$ branched alkyl, $C_2$–$C_{22}$ alkenyl, $C_3$–$C_{22}$ branched alkenyl;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl;
f) polyhydroxyl substituted $C_3$–$C_{22}$ alkyl;
g) C 1–$C_{22}$ alkoxy, preferably $C_1$–$C_4$ alkoxy, more preferred methoxy;
h) branched alkoxy having the formula

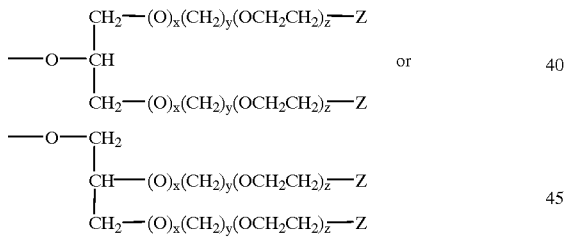 or wherein Z is hydrogen, hydroxyl, $C_1$–$C_{30}$ linear alkyl, $C_1$–$C_{30}$ branched alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, preferably from 0 to 6; each z independently has the value from 0 to 100, preferably from 0 to about 10, more preferably from 0 to about 3;

i) substituted aryl, and unsubstituted aryl having the formula:

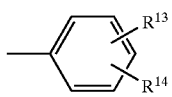

wherein $R^{13}$ and $R^{14}$ are independently selected from the group consisting of hydrogen, $C_1$–$C_6$ alkyl, $C_3$–$C_6$ alkenyl, $C_1$–$C_6$ alkoxy, $C_3$–$C_6$ branched alkoxy, halogen, —$CO_2^-M^+$, —$SO_3^-M^+$, —$OSO_3^-M^+$, —$N(R^{15})_2$, and —$N^+(R^{15})_3X^-$ wherein each $R^{15}$ is independently hydrogen or $C_1$–$C_4$ alkyl; and mixtures thereof; preferably hydrogen $C_1$–$C_6$ alkyl, —$CO_2^-M^+$, —$SO_3^-M^+$, —$OSO_3^-M^+$, and mixtures thereof, more preferably $R^{13}$ or $R^{14}$ is hydrogen and the other moiety is $C_1$–$C_6$ alkyl; wherein M is a water soluble cation and X is a water soluble anion.

j) substituted alkylenearyl and unsubstituted alkylenearyl having the formula:

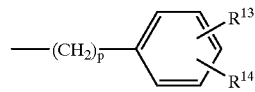

wherein $R^{13}$ and $R^{14}$ are as defined above, p is from 1 to about 10.

k) substituted aryloxy and unsubstituted aryloxy having the formula:

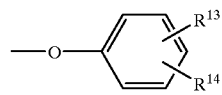

wherein $R^{13}$ and $R^{14}$ are as defined above.

l) substituted alkyleneoxyaryl and unsubstituted alkyleneoxyaryl units are defined as moieties having the formula:

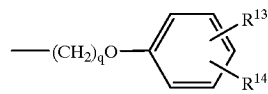

wherein $R^{13}$ and $R^{14}$ are as defined above, q is from 0 to about 10.

m) substituted oxyalkylenearyl and unsubstituted oxyalkylenearyl having the formula:

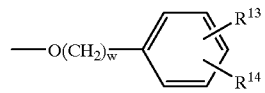

wherein $R^{13}$ and $R^{14}$ are as defined above, w is from about 1 to about 10.

n) $C_1$–$C_{22}$ linear, $C_3$–$C_{22}$ branched thioalkyl, $C_1$–$C_{22}$ linear, $C_3$–$C_{22}$ branched substituted thioalkyl, and mixtures thereof;

o) carboxylate units of the formula

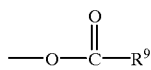

wherein $R^9$ is $C_1$–$C_{22}$ alkyl, $C_3$–$C_{22}$ branched alkyl, $C_2$–$C_{22}$ alkenyl, $C_3$–$C_{22}$ branched alkenyl, all of which can be substituted with halogen; poly-hydroxyl substituted $C_3$–$C_{22}$ alkyl, $C_3$–$C_{22}$ glycol; $C_1$–$C_{22}$ alkoxy, $C_3$–$C_{22}$ branched alkoxy; substituted and unsubstituted aryl, alkylenearyl, aryloxy, oxyalkylenearyl, alkyleneoxyaryl; preferably $C_1$–$C_{22}$ alkyl, $C_3$–$C_{22}$ branched alkyl, and mixtures thereof;

p) alkyleneamino units having the formula:

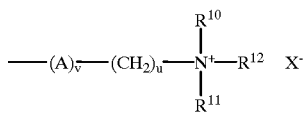

wherein $R^{10}$, and $R^{11}$ are each a $C_1$–$C_{22}$ alkyl, $C_3$–$C_{22}$ branched alkyl, $C_2$–$C_{22}$ alkenyl, $C_3$–$C_{22}$ branched alkenyl, $R^{12}$ is hydrogen, $C_1$–$C_{22}$ alkyl, $C_3$–$C_{22}$ branched alkyl, $C_2$–$C_{22}$ alkenyl, $C_3$–$C_{22}$ branched alkenyl and mixtures thereof, the index v is 0 or 1; X is a other water soluble anion, u is from 0 to 22, preferably u is from 3 to about 10. Examples of water soluble anions include organic species such as fumarate, tartrate, oxalate and the like, inorganic species include chloride, bromide, sulfate, hydrogen sulfate, phosphate and the like;

q) an amino unit of the formula

wherein $R^{17}$ and $R^{18}$ are each a $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) alkylethyleneoxy units having the formula:

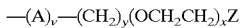

wherein Z is hydrogen, hydroxyl, —$CO_2H$, —$SO_3^-M^+$, —$OSO_3^-M^+$, $C_1$–$C_6$ alkoxy, substituted and unsubstituted aryl, substituted and unsubstituted aryloxy; alkyleneamino as defined herein above; or mixtures thereof; A units comprise nitrogen or oxygen, preferably oxygen; M is a water soluble cation; v is 0 or 1; x is from 0 to 100, preferably from 0 to 20, more preferably from 0 to 5; y is from 0 to 12, preferably from 1 to 4; however, no peroxide —O—O— bonds are contained within the photobleaching compounds of the present invention;

s) siloxy and substituted siloxy of the formula —$OSiR^{19}R^{20}R^{21}$ wherein each $R^{19}$, $R^{20}$, and $R^{21}$ is independently selected from the group consisting of $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof, substituted or unsubstituted aryl, aryloxy; alkylethyleneoxy units of the formula:

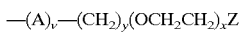

wherein Z is hydrogen, hydroxyl, $C_1$–$C_{30}$ alkyl, —$CO_2H$, —$SO_3^-M^+$, —$OSO_3^-M^+$, $C_1$–$C_6$ alkoxy; substituted or unsubstituted aryl, and aryloxy; alkyleneamino as defined herein above, and mixtures thereof, preferably hydrogen or $C_1$–$C_6$ alkyl, more preferably methyl; v is 0 or 1; x is from 1 to 100, preferably from 0 to about 20, more preferably from 3 to about 10; and y is from 0 to 12, preferably from about 0 to about 5.

According to the present invention the preferred axial R units comprise moieties having the formula

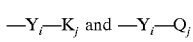

wherein

Y is a linking moiety selected from the group consisting of O, $CR^{25}R^{26}$, $OSiR^{25}R^{26}$, $OSnR^{25}R^{26}$, and mixtures thereof; wherein $R^{25}$ and $R^{26}$ are hydrogen, $C_1$–$C_4$ alkyl, halogen, and mixtures thereof; i is 0 or 1, j is from 1 to 3;

K is a ligand selected from the group consisting of:
a) $C_1$–$C_{30}$ linear alkyl, $C_3$–$C_{30}$ branched alkyl, $C_2$–$C_{30}$ linear alkenyl, $C_3$–$C_{30}$ branched alkenyl, $C_6$–$C_{20}$ aryl, $C_7$–$C_{20}$ arylalkyl, $C_7$–$C_{20}$ alkylaryl, and mixtures thereof;
b) an alkylethyleneoxy unit of the formula

wherein Z is selected from the group consisting of hydrogen, $C_1$–$C_{20}$ alkyl, $C_3$–$C_{20}$ branched alkyl, $C_2$–$C_{20}$ linear alkenyl, $C_3$–$C_{20}$ branched alkenyl, $C_6$–$C_{20}$ aryl, $C_7$–$C_{30}$ arylalkyl, $C_6$–$C_{20}$ alkylaryl, and mixtures thereof; $R^{22}$ is selected from the group consisting of $C_1$–$C_4$ linear alkylene, $C_3$–$C_4$ branched alkylene, $C_3$–$C_6$ hydroxyalkylene, and mixtures thereof; $R^{23}$ is selected from the group consisting of $C_2$–$C_{20}$ alkylene, $C_3$–$C_{20}$ branched alkylene, $C_6$–$C_{20}$ arylene, $C_7$–$C_{30}$ arylalkylene, $C_7$–$C_{30}$ alkylarylene, and mixtures thereof; x is from 1 to 100; y is 0 or 1; and Q is an ionic moiety having the formula:

wherein $R^{24}$ is selected from the group consisting of $C_3$–$C_{30}$ linear alkylene, $C_3$–$C_{30}$ branched alkylene, $C_2$–$C_{30}$ linear alkenylene, $C_3$–$C_{30}$ branched alkenylene, $C_6$–$C_{16}$ arylene, and mixtures thereof; W is selected from the group consisting of —$CO_2^-M^+$, —$SO_3^-M^+$, —$OSO_3^-M^+$; $PO_3^{2-}M^+$, —$OPO_3^-M^+$, —$N^+(R^{27})_3X^-$; wherein $R^{27}$ is independently hydrogen, $C_1$–$C_6$ alkyl, —$(CH_2)_nOH$, —$(CH_2CH_2O)_nH$, and mixtures thereof; wherein n is from 1 to 4; M is a water soluble cation of sufficient charge to provide electronic neutrality and X is a water soluble anion as defined herein above.

Preferred axial R units are alkyl alkyleneoxy units of the formula

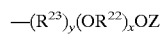

wherein Z is selected from the group consisting of hydrogen, $C_7$–$C_{20}$ linear alkyl, $C_3$–$C_{20}$ branched alkyl, $C_2$–$C_{20}$ linear alkenyl, $C_3$–$C_{20}$ branched alkenyl, $C_6$–$C_{10}$ aryl, $C_7$–$C_{20}$ arylalkyl, $C_7$–$C_{20}$ alkylaryl, and mixtures thereof; $R^{22}$ is selected from the group consisting of $C_1$–$C_4$ linear alkylene, $C_3$–$C_4$ branched alkylene, and mixtures thereof; $R^{23}$ is selected from the group consisting of $C_2$–$C_6$ alkylene, $C_3$–$C_6$ branched alkylene, $C_6$–$C_{10}$ arylene, and mixtures thereof; x is from 1 to 50; y is 0 or 1.

More preferred axial R units comprise y equal to 0, Z is hydrogen, $C_1$–$C_{20}$ alkyl, $C_3$–$C_{20}$ branched alkyl, $C_6$–$C_{10}$ aryl, and mixtures thereof, most preferred Z is hydrogen or $C_6$–$C_{20}$ linear alkyl, $C_{10}$–$C_{20}$ branched alkyl; $R^{22}$ is $C_1$–$C_4$ linear or $C_3$–$C_4$ branched alkylene.

Also preferred R units having the formula:

wherein Y is a linking moiety selected from the group consisting of O, $CR^{25}R^{26}$ $OSiR^{25}R^{26}$, $OSnR^{25}R^{26}$, and mixtures thereof; i is 0 or 1, j is from 1 to 3; Q is an ionic moiety having the formula:

—R²⁴—W wherein $R^{24}$ is selected from the group consisting of $C_2$–$C_{20}$ linear alkylene, $C_3$–$C_{20}$ branched alkylene, $C_2$–$C_{20}$ linear alkenylene, $C_3$–$C_{20}$ branched alkenylene, $C_6$–$C_{10}$ arylene, and mixtures thereof; W is selected from the group consisting of —$CO_2^-M^+$, —$SO_3^-M^+$, —$OSO_3^-M^+$; $PO_3^{2-}M^+$, —$OPO_3^-M^+$, —$N^+(R^{27})_3X^-$; wherein $R^{27}$ is independently hydrogen, $C_1$–$C_6$ alkyl, —$(CH_2)_nOH$, —$(CH_2CH_2O)_nH$, and mixtures thereof; wherein n is from 1 to 4; M is a water soluble cation of sufficient charge to provide electronic neutrality and X is a water soluble anion as defined herein above.

A preferred hydrophilic R has the index i equal to 1; $R^{24}$ is $C_3$–$C_{20}$ linear alkylene, $C_3$–$C_{20}$ branched alkylene; W is —$CO_2^-M^+$, —$SO_3^-M^+$, —$OSO_3^-M^+$; M is a water soluble cation of sufficient charge to provide electronic neutrality.

Examples of Y units suitable for use in R units having the formula:

—$Y_i$—$K_j$ have the formula

—O—$K^1$, —$S_n$—$K^1$, —OSn—$K^1$ wherein i is equal to 1 and j is equal to 1. Further examples have the formula

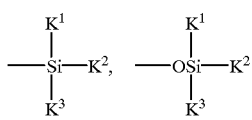

wherein i is equal to 1 and j is equal to 3. The above examples also apply to Y units when used with Q ionic moieties.

When compounds of the present invention have present one or more substituent $R^1$, $R^2$, $R^3$, and $R^4$, units, as in the case of phthalocyanine, or $R^1$, $R^2$, $R^3$, $R^4$, $R^5$, and $R^6$ units, as in the case of naphthalocyanines, the exact orientation of the substituents may not be exactly known. However, for the purposes of the compounds of the present invention, certain equivalencies of substitution exist. For example, the two units of the following formula

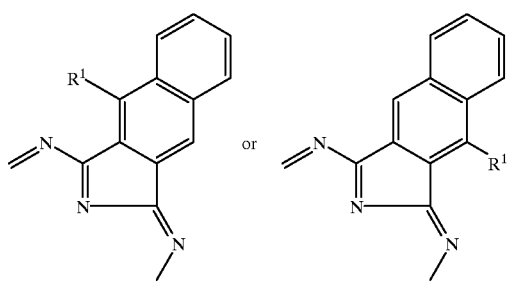

which contain the same $R^1$ substitution, are equivalent for the purposes of the present invention and the selection of either one structure over the other will not effect the desired properties of the molecule described herein.

In addition, compounds containing the substitution represented by the following formulas

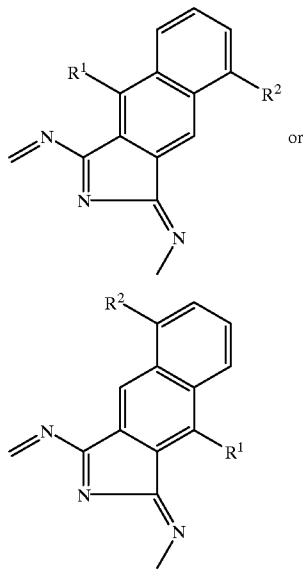

which contain the same $R^1$ and $R^2$ unit substitutions, are also equivalent for the purposes of the present invention and the selection of either one structure over the other will not effect the desired properties of the molecule described herein. The above examples, however, are only representative of the total number of equivalent structure examples that will be recognized by those skilled in the art.

Compounds useful for the present invention having substituted one or more $R^1$, $R^2$, $R^3$, and $R^4$, unit, as in the case of phthalocyanine, or $R^1$, $R^2$, $R^3$, $R^4$, $R^5$, and $R^6$ unit, as in the case of naphthalocyanines, which have their substitutions oriented in a manner described by the following formula

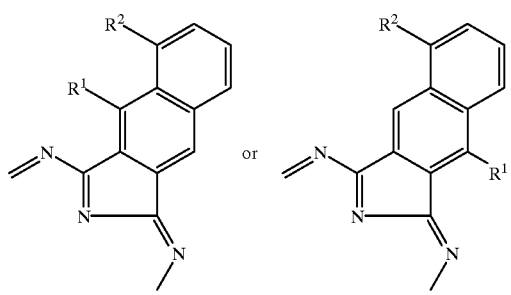

are not equivalent for the purposes of the present invention and would each constitute separate compounds regardless of the fact that the $R^1$ and $R^2$ units are equivalent. The above example does not exhaust the number of non-equivalent structures that are possible using any combination of $R^1$, $R^2$, $R^3$, $R^4$, $R^5$, and $R^6$ units recognized by those skilled in the art.

Solublizing axial R units, are bonded directly to the central tin, germanium, platinum or palladium atom. Each R unit can be chosen independently of the other. The selection of an R unit is made, for example, to provide solubility, non-solubility, "substantivity", "non-substantivity" to the compound. These are a few examples of the utility of the axial group and those skilled in the art will recognize that other properties of the photobleaches can be controlled via axial substitution. R units are nonionic, cationic, or anionic units.

Below is an example of a preferred "substantive" embodiment (has an affinity for surfaces, e.g. fabric) of the present invention comprising a phthalocyanine ring system wherein at least one of the $R^1$, $R^2$, $R^3$, and $R^4$ units of each aromatic moiety is methoxy, each R group comprises an ethyleneoxy unit of the formula

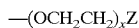
—(OCH$_2$CH$_2$)$_x$Z wherein for each R unit Z is methoxy and x is 7.2 thereby giving the moiety an average ethoxylation value of 7.2.

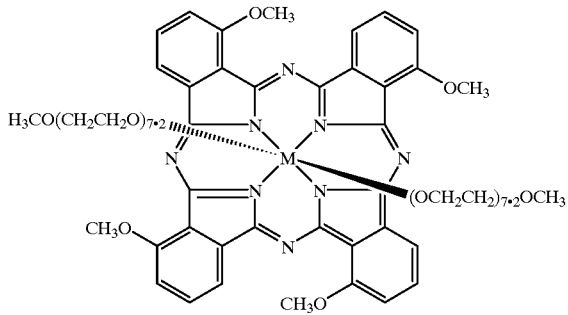

Below is an example of a "substantive" embodiment (has an affinity for surfaces, e.g. fabric) of the present invention comprising a phthalocyanine ring system wherein at least two of the $R^1$, $R^2$, $R^3$, and $R^4$ units of each aromatic moiety is methoxy, each R group comprises an ethyleneoxy unit of the formula

—(OCH$_2$CH$_2$)$_x$Z wherein for each R unit Z is methoxy and x is 7.2 thereby giving the moiety an average ethoxylation value of 7.2.

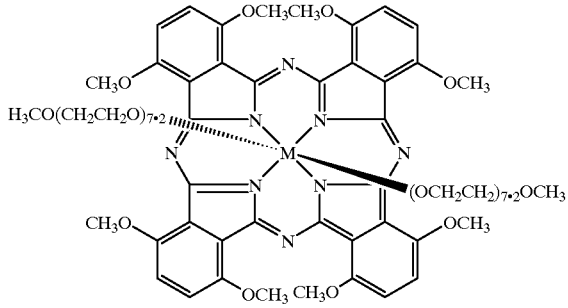

Below is an example of a "non-substantive" embodiment (charged R units reduces the affinity for surfaces, e.g. fabric) of the present invention comprising a naphthalocyanine ring system wherein at least two of the $R^1$, $R^2$, $R^3$, $R^4$, $R^5$, and $R^6$ units of each aromatic moiety are chlorine, one R group comprises an siloxy unit the formula —OSiR$^7$R$^8$R$^9$ wherein $R^7$ and $R^8$ units are methyl and $R^9$ is of the formula

—(CH$_2$)$_y$Z wherein Z is —SO$_3^-$M$^+$, M is sodium and y is equal to six; the second axial R unit is methoxy.

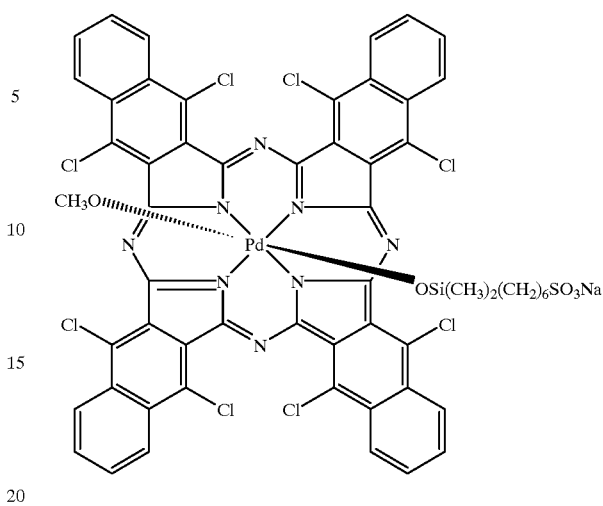

Below is an example of a "non-substantive" embodiment (charged R units reduces the affinity for surfaces, e.g. fabric) of the present invention comprising a naphthalocyanine ring system wherein at least one of the $R^1$, $R^2$, $R^3$, $R^4$, $R^5$, and $R^6$ units of each aromatic moiety is bromine, and the R groups comprise an siloxy unit the formula —OSiR$^7$R$^8$R$^9$ wherein $R^7$ and $R^8$ units are methyl and $R^9$ is of the formula

—(CH$_2$)$_y$Z wherein Z is —SO$_3^-$M$^+$, M is sodium and y is equal to six.

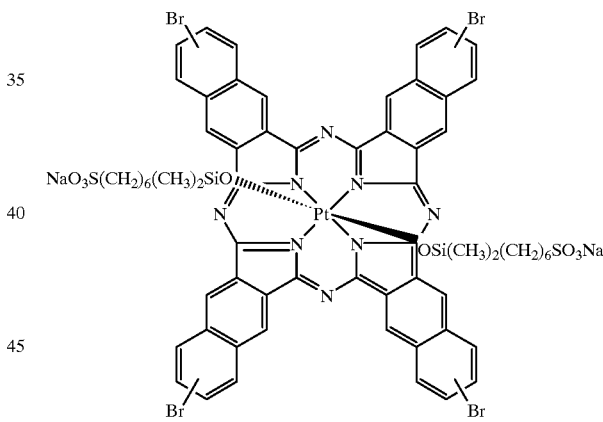

The compounds of the present invention can be modified to have a wide range of surface affinities. Molecules can be made "substantive" or "non-substantive" by the choice of axial R units. The term "substantivity" as defined herein is the property which allows the photobleaching agent to successfully deposit on a targeted surface. For example, the axial groups R, hereinafter defined in the specification, may be selected to provide compatibility of the photobleaching compound with a synthetic fabric, a durable surface such as ceramic tile, or in general any fabric, article of manufacture or situs that is to be a target of photobleaching.

The present invention also relates to laundry detergent or hard surface cleaning compositions comprising:
   A) at least about 0.1%, preferably from about 0.1% to about 30%, more preferably from about 1% to about 30%, most preferably from about 5% to about 20% by weight, of a detersive surfactant, said detersive surfactant is selected from the group consisting of anionic, cationic, nonionic, zwitterionic, ampholytic surfactants, and mixtures thereof;

B) at least about 0.001 ppm, preferably from about 0.01 to about 10000 ppm, more preferably from about 0.1 to about 5000 ppm, most preferably form about 10 to about 1000 ppm, of a photosensitizing compound having a Q-band maximum absorption wavelength of 660 nanometers or greater according to the present invention; and C) the balance carriers and adjunct materials.

The present invention further relates to laundry detergent or hard surface cleaning compositions comprising:

A) at least about 0.1%, preferably from about 0.1% to about 30%, more preferably from about 1% to about 30%, most preferably from about 5% to about 20% by weight, of a detersive surfactant, said detersive surfactant is selected from the group consisting of anionic, cationic, nonionic, zwitterionic, ampholytic surfactants, and mixtures thereof;

B) at least about 0.001 ppm, preferably from about 0.01 to about 10000 ppm, more preferably from about 0.1 to about 5000 ppm, most preferably form about 10 to about 1000 ppm, of a photosensitizing compound having a Q-band maximum absorption wavelength of 660 nanometers or greater according to the present invention; wherein selection of a suitable moiety for a $R^1, R^2, R^3, R^4, R^5$, or $R^6$ substituent is capable of providing the photobleach or photodisinfectant with a positive Δtriplet yield of at least 1, preferably at least 10, more preferably at least 30, when said moiety replaces a hydrogen atom; and C) the balance carriers and adjunct materials.

The present invention yet further relates to laundry detergent and hard surface cleaning compositions comprising:

A) at least about 0.1%, preferably from about 0.1% to about 30%, more preferably from about 1% to about 30%, most preferably from about 5% to about 20% by weight, of a detersive surfactant, said detersive surfactant is selected from the group consisting of anionic, cationic, nonionic, zwitterionic, ampholytic surfactants, and mixtures thereof;

B) at least about 0.001 ppm, preferably from about 0.01 to about 10000 ppm, more preferably from about 0.1 to about 5000 ppm, most preferably form about 10 to about 1000 ppm, of a photosensitizing compound having a Q-band maximum absorption wavelength of 660 nanometers or greater according to the present invention; wherein selection of a suitable moiety for a $R^1, R^2, R^3, R^4, R^5$, or $R^6$ substituent is capable of providing a positive red shift value of at least 1, preferably a positive red shift value of at least 10, more preferrably a positive red shift value of at least 30, when said moieties are substituted for hydrogen; and C) the balance carriers and adjunct materials Selection of a specific R moiety is generally made for adjustment of the solubility or substantivity of the molecule. For example, the R unit is matched to the structural properties of either the targeted material (i.e. fabric) or to the targeted substrate (i.e. stain). The option to tailor the properties of the R unit to the material, is due to the ability to select R units independently of effecting the phthalocyanine or naphthalocyanine ring.

An additional benefit of the photobleaching system of the present invention is that they are generally more fabric and color safe than conventional bleaches (i.e. hypochlorite).

"Non-substantive" molecules are desirable for applications where the photosensitizing compound must remain in the liquor rather than becoming attracted to a particular surface, i.e. water sterilization.

The term "low hue" as used herein and throughout the specification refers to photobleaches that have a $\lambda_{max}$ of their Q-band above about 700 nm and are therefore only slightly perceptible to the human eye. Those additional materials of the present invention having Q-band maximum wavelengths in the "visible" range, (i.e. 660–700 nanometers) are materials that are most suitable when the perception of a colored material is not a factor in deterring utility.

Effective photobleaching is predicated on the production of a molecule of singlet oxygen, a theory which has been extensively studied and is well understood by those skilled in the art of photobleaching. Because the singlet oxygen species is short-lived, having the photosensitizing molecule in proximity to the stain or the microbe to be "attacked" is of primary advantage.

The molecules of the present invention because of the ability of the formulator to control "substantivity", can be directed to any desired surface. The additional ability to prevent layering and stacking of photosensitizing molecules due to the axial nature of the R units, provides for an efficient mono-layer. For example, an embodiment of the present invention for removing stains from a fabric will have the requirements that the organotin, organogermanium, organoplatinum, organopalladium, organolead, or organophosphorous photosensitizing compound have an affinity for the fabric surface, and that the photobleaching compound be close to the desired site of action. These requirements are achieved by manipulation of one or more R units.

The present invention also relates to a process for carrying out a photo-sensitized reaction or a reaction catalyzed by singlet oxygen, wherein one or more phthalocyanine or naphthylocyanine compounds in the presence of oxygen, are brought into contact with the medium in which or on which the said reaction is to take place, or are incorporated in this medium, and are irradiated with light.

It has long been known that phthalocyanine and naphthalocyanine rings, can absorb light quanta and form electronically excited species (singlet and triplet) and that these species can be quenched by oxygen to yield 'excited oxygen species'. A particularly preferred 'excited oxygen species' is singlet oxygen which is most reliably formed by the quenching of the triplet state of a photosensitizer, such as a phthalocyanine, by molecular oxygen. It is therefore an aim of the photobleach formulator to produce compounds that favor the formation of the triplet state.

When a photosensitizer is irradiated with light, the singlet energy state that results undergoes a variety of processes i.e. re-emission of light (fluorescence). The most important process with regard to photobleaching via singlet oxygen is inter system crossing (ISC). This is the mechanism by which the singlet state is converted to the triplet state. In general, the efficiency of this process is discussed in terms of quantum yield, i.e. the number of photons absorbed that lead to the desired triplet excited state. The present invention provides for increased photobleaching by modifying the efficiency of inter system crossing from the singlet state to the triplet state. The molecules of the present invention, can be modified by the formulator to increase the quantum efficiency of triplet formation via the "heavy atom effect". The selection of a moiety for its "heavy atom effect" can be made independently of other factors, for example, without undue concern for solubility factors. This is because the choice of axial R groups for solubility will have no bearing on the changes made to the phthalocyanine or naphthalocyanine ring system.

The determination of the value of the Q-band wavelength and whether a shift occurs in this wavelength when a particular moiety ($R^1$, $R^2$, $R^3$, $R^4$, $R^5$ or $R^6$ unit) replaces a hydrogen atom on the phthalocyanine or naphthalocyanine ring is straight-forward. Typically, a solution having a concentration of approximately $1 \times 10^{-6}$ M of the phthalocyanine or naphthalocyanine to be measured is prepared using a suitable solvent (e.g. dimethylformamide) which contains 1 wt % triton X-100. A UV/visible spectrum is then obtained and the Q-band $\lambda_{max}$ is recorded. This value is the "substrate $\lambda_{s-max}$". A spectrum for the material prior to introduction of the substituent group is obtained in the same manner. This value is the "reference $\lambda_{r-max}$". The two spectra are compared and the resulting measured values are placed into the following equation wavelength red shift=$\Delta\lambda_{max}=\lambda_{s-max}-\lambda_{r-max}$ wherein if the number obtained is greater than or equal to 1, then the substituent group has produced a positive red shift of at least one nanometer and the substituent is a preferred embodiments of the present invention. If the material of interest is not soluble in dimethylformamide another suitable solvent may be used.

Quantum yields and excited state energies are well known to those skilled in the art and the procedures for the determination of triplet quantum yield and like photophysical parameters are thoroughly described in the following references Bonnet, R.; McGarvey, D. J.; Harriman, A.; Land, E. J.; Truscott, T. G.; Winfield, U-J. Photochem. Photobiol. 1988, 48 (3), pg. 271–6; Davila, J., Harriman, A., Gulliya, K. S., Photochem. Photobiol., 1991, 53 (1), pg. 1–11; Davila, J., Harriman, A., Photochem. Photobiol., 1989, 50 (1), pg. 29–35; Charlesworth, P., Truscottt, T. G., Brooks, R. C., Wilson, B. C., J. Photochem, Photobiol., part B 1994, 26 (3), pg. 277–82; Zhang, X., Xu, H., J. Chem. Soc., Faraday Trans., 1993, 89 (18), pg. 3347–51; Simpson, M. S. C., Beeby, A., Bishop, S. M., MacRobert, A. J., Parker, A. W., Phillips, D., Proc. SPIE-int. Soc. Opt. Eng., 1992, 1640, pg. 520–9; Phillips, D., Pure Appl. Chem., 1995, 67 (1), pg. 117–26; Wilkinson, F., Helman, W. P., Ross, A. B., J. Phys. Chem. Ref. Data, 1993, 22 (1), pg. 113–262; Lever, A. P. B., Licoccia, S., Magnell, K., Minor, P. C., Ramaswamy, B. S., Adv. Chem. Ser., 1982, 201, pg. 237–52; West, M. A., Creat. Detect. Excited State, 1976, 4, pg. 217–307; Ford, W. E., Rihter, B. D., Kenney, M. E., Rodgers, M. A. J., Photochem. PhotobioL, 1989, 50 (3), pg. 277–282; Firey, P. A., Ford, W. E., Sounik, J. R., Kenney, M. E., Rodgers, A. J. R., J. Am. Chem. Soc., 1988, 110, pg. 7626–7630; Firey, P. A., Rodgers, M. A. J., Photochem. Photobiol., 1987, 45 (4), pg. 535–8; all of which are incorporated by reference in their entirety.

For the purposes of the present invention the delta triplet yield is determined by determining the % quantum yield of triplet fro the phthalocyanine or naphthalocyanine of interest and this is the term $\phi_{trip-substrate}$. The % quantum yield of triplet for the phthalocyanine or naphthalocyanine prior to introduction of the substituent is determine. This value is $\phi_{trip-reference}$. The value are place in the following equation triplet state quantum yield increase=$\Delta\phi_{trip}=\phi_{trip-substrate}-\phi_{trip-reference}$ When the value for $\Delta\phi_{trip}$ is a number greater than or equal to 1, the substitution made therein for a hydrogen atom on the (Sens.) unit of the photosensitizer is a preferred embodiments of the present invention.

In particular, the present invention relates to process for bleaching or removing stains from textiles, organic or inorganic substrates. It is further an object of the present invention to protect the latter against attack by microorganisms, wherein the substrates are treated with phthalocyanines or naphthalocyanines of the present invention, in the presence of water and while being irradiated by light.

Another advantage of the present invention is the fact that each R unit may be directed toward a separate desired property and the molecules of the present invention can therefore be thought of as being "sided". For example, one axial R unit may be direct toward increased solubility while the other axial R group may be chosen for its ability to provide increase substantivity.

The present invention also relates to a process for carrying out a photo-sensitized reaction or a reaction catalyzed by singlet oxygen, wherein one or more phthalocyanine or naphthylocyanine compounds in the presence of oxygen, are brought into contact with the medium in which or on which the said reaction is to take place, or are incorporated in this medium, and are irradiated with light.

If the method is carried out in an aqueous medium (for example the sterilization of textiles), the irradiation with light can either be carried out directly in the treatment medium by means of an artificial source of light mounted inside or outside the medium or the substrates, in a moist state, can subsequently either be irradiated, again by means of an artificial source of light, or can be exposed to sunlight. Good antimicrobial effects of the present compounds can be achieved even with very low concentrations of active substance, for example at 0.001 ppm. Depending on the field of use and on the phthalocyanine or naphthylocyanine derivative employed, a concentration between 0.005 and 100, preferably 0.01 and 50 ppm is preferable. The irradiation can be effected by means of an artificial source of light or by means of sunlight. The intensity of the illumination can vary within wide limits, and it depends both on the concentration of active as well as the nature of the light source as to the photobleaching efficiency of any particular compound of the present invention. A further parameter which can be varied is the exposure time, i.e. for the same effect exposure must be longer at a lower light intensity than at a higher intensity. In general, depending on the field of use, exposure time of a few minutes up to a few hours is possible.

If the process is carried out in an aqueous medium (for example the sterilization of textiles), the irradiation with light can either be carried out directly in the treatment medium, by means of an artificial source of light mounted inside or outside the medium, or the articles, in a moist state, can subsequently either be irradiated, again by means of an artificial source of light, or can be exposed to sunlight. Good antimicrobial effects con be achieved even with very low concentrations of active substance, for example at 0.001 ppm. Depending on the field of use and on the phthalocyanine or naphthylocyanine derivative employed, a concentration between 0.005 and 2000, preferably 0.01 and 1000 ppm is preferable.

The methods of the present invention can also be accomplished in solvent based carriers or in low aqueous solutions. For the purpose of the present invention the term low aqueous means that water is added to a carrier system to modify the properties of the carrier and not solely for the purpose of solublizing the substrate. For example, solvents that are capable of holding solublized oxygen as well as forming a miscible system with water are preferred. Non-limiting examples of these solvents are butoxy propoxy propanol (BPP), methoxy propoxy propanol (MPP), ethoxy propoxy propanol (EPP), and propoxy propoxy propanol (PPP). Embodiments of the present invention which comprise these non-classical aqueous compositions are most useful when the photobleach must be applied to a woven fabric or surface that contains agents which repel water and moisture.

The sterilization of textiles of synthetic or natural original may be mentioned as an important application. Thus, material to be washed in the household or in industry can be disinfected by means of the methods of the present invention. The material to be washed can be treated for this purpose in the manner mentioned above with aqueous solutions of the phthalocyanines or naphthalocyanines of the present invention while being irradiated with light. The phthalocyanine and naphthalocyanines can advantageously be present in the treatment medium in a concentration of from 0.01 to about 2000 mg per liter, preferably from 0.1 to 1000, more preferably from 1 to 500. The sterilization can be carried out advantageously together with the washing process. For this purpose, the material to be washed is treated with a wash medium containing customary detergent substances, one or more phthalocyanines or naphthalocyanines according to the present invention and, if desired, inorganic salts and/or other adjunct materials having antimicrobial properties. The washing process con be carried out manually, for example in a tub, or can be carried out in a washing machine. The necessary exposure to light can be effected during the washing process by means of suitable light sources, or the moist material being washed can also, subsequently, for example during drying, either be exposed to a suitable artificial source of light or simply exposed to sunlight, for example line drying.

Surface bleaching can be achieved, for example by applying to the appropriate surface, an aqueous solution of the phthalocyanine or naphthalocyanine compound according to the present invention, this solution preferably comprising from about 0.001 to about 10%, by weight of active substance. The solution can also comprise, in addition, other customary additives, for example wetting agents, dispersing agents or emulsifiers, detergent substances and, if desired inorganic salts. After this solution has been applied, the surface is simply exposed to sunlight or, if required, it can in addition be irradiated by means of an artificial source of light. It is advisable to keep the surface moist during the exposure to light.

The laundry compositions of the present invention optionally comprise detersive surfactants, examples of which are, anionic, cationic, nonionic, amphoteric and zwitterionic, however the formulator is not limited to these examples or combinations thereof. The surfactants are present from about 0% to about 95%, preferably from about 5% to about 30%, by weight of the composition.

The cleaning compositions of the present invention optionally comprise detersive surfactants, examples of which are, anionic, cationic, nonionic, amphoteric and zwitterionic, however the formulator is not limited to these examples or combinations thereof. The surfactants are present from about 0% to about 50%, preferably from about 5% to about 30%, by weight of the composition.

The laundry compositions of the present invention optionally contains builders, examples of which are, silicates, carbonates, and zeolites, however the user is not limited to these examples or combinations thereof. The builders are present from about 0% to about 50%, preferably from about 5% to about 30%, by weight of the composition.

The cleaning compositions of the present invention optionally contains builders, examples of which are, silicates, carbonates, and zeolites, however the user is not limited to these examples or combinations thereof. The builders are present from about 0% to about 50%, preferably from about 5% to about 30%, by weight of the composition.

The hard surface cleaner of the present invention optionally contains builders, examples of which are, silicates, carbonates, and zeolites, however the user is not limited to these examples or combinations thereof. The builders are present from about 0% to about 50%, preferably from about 5% to about 30%, by weight of the composition.

The hard surface cleaner of the present invention optionally contains abrasives from about 0.5% to about 85%, preferably from about 10% to about 85%, by weight of the composition. Suitable abrasives are silicates, carbonates, perlite, clay, and pulverized ceramic clay, however, the user is not restricted to these examples or combinations thereof.

Substances which increase the action can also be added in the process according to the invention, inter alia electrolytes, for example inorganic salts, for instance sodium chloride, potassium chloride, sodium sulfate, potassium sulfate, sodium acetate ammonium acetate, alkali metal phosphates and alkali metal tri-polyphosphates, especially sodium chloride and sodium sulfate. These salts can be added to the agents according to the invention or can be added directly in the application method, so that they are present in the application solution in a concentration of, preferably 0.1 to 10%, by weight.

What is meant by the term aqueous solution is a solution that is essentially water, however the formulator may include adjunct materials as well as a surfactant to aid in removal of the "treated" micro organisms during rinsing or subsequent cleaning. The presence of an aqueous solution facilitates the production of singlet oxygen due to the higher concentration of oxygen in water than in air.

Surfactant

The instant cleaning compositions contain from about 0.1% to about 60% by weight of a surfactant selected from the group consisting of anionic, nonionic, ampholytic and zwitterinonic surface active agents. For liquid systems, surfactant is preferably present to the extent of from about 0.1% to 20% by weight of the composition. For solid (i.e. granular) and viscous semi-solid (i.e. gelatinous, pastes, etc.) systems, surfactant is preferably present to the extent of from about 1.5% to 30% by weight of the composition.

Nonlimiting examples of surfactants useful herein typically at levels from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid anides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are described further herein and are listed in standard texts.

Anionic surfactants can be broadly described as the water-soluble salts, particularly the alkali metal salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic synthetic detergents which can form the surfactant component of the compositions of the present invention are the sodium or potassium alkyl sulfates, especially those obtained by sulfating the higher alcohols (C8–18 carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid ester of the reaction product of one mole of a higher fatty alcohol (e.g. tallow or coconut alcohols) and about 1 to about 10 moles of ethylene oxide; sodium or potassium salts of alkyl phenol ethylene oxide ether sulfates with about 1 to about 10 units of ethylene oxide per molecule and in which the alkyl radicals contain from 8 to 12 carbon atoms; the reaction products of fatty acids are derived from coconut oil sodium or potassium salts of fatty acid amides of a methyl tauride in which the fatty acids, for example, are derived from coconut oil and sodium or potassium beta-acetoxy- or beta-acetamido-alkanesulfonates where the alkane has from 8 to 22 carbon atoms.

Additionally, secondary alkyl sulfates may be used by the formulator exclusively or in conjunction with other surfactant materials and the following identifies and illustrates the differences between sulfated surfactants and otherwise conventional alkyl sulfate surfactants. Non-limiting examples of such ingredients are as follows.

Conventional primary alkyl sulfates (LAS), such as those illustrated above, have the general formula ROSO3-M+ wherein R is typically a linear C8-22 hydrocarbyl group and M is a water solublizing cation, for example sodium LAS. Branched chain primary alkyl sulfate surfactants (i.e., branched-chain "PAS") having 8–20 carbon atoms are also know; see, for example, Eur. Pat. Appl. 439,316, Smith et al., filed Jan. 21, 1991.

Conventional secondary alkyl sulfate surfactants are those materials which have the sulfate moiety distributed randomly along the hydrocarbyl "backbone" of the molecule. Such materials may be depicted by the structure

wherein m and n are integers of 2 of greater and the sum of m+n is typically about 9 to 17, and M is a water-solublizing cation.

The aforementioned secondary alkyl sulfates are those prepared by the addition of $H_2SO_4$ to olefins. A typical synthesis using alpha olefins and sulfuric acid is disclosed in U.S. Pat. No. 3,234,258, Morris, issued Feb. 8, 1966 or in U.S. Pat. No. 5,075,041, Lutz, issued Dec. 24, 1991. The synthesis conducted in solvents which afford the secondary (2,3) alkyl sulfates on cooling, yields products which, when purified to remove the unreacted materials, randomly sulfated materials, unsulfated by-products such as C10 and higher alcohols, secondary olefin sulfonates, and the like, are typically 90+% pure mixtures of 2- and 3-sulfated materials (some sodium sulfate may be present) and are white, non tacky, apparently crystalline, solids. Some 2,3-disulfates may also be present, but generally comprise no more than 5% of the mixture of secondary (2,3) alkyl mono-sulfates. Such materials are available as under the name "DAN", e.g., "DAN 200" from Shell Oil Company.

Bleaching Agents and Bleach Activators

The detergent compositions herein may optionally contain bleaching agents or bleaching compositions containing a bleaching agent and one or more bleach activators. When present, bleaching agents will typically be at levels of from about 1% to about 30%, more typically from about 5% to about 20%, of the detergent composition, especially for fabric laundering. If present, the amount of bleach activators will typically be from about 0.1% to about 60%, more typically from about 0.5% to about 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches other than the hypohalite (e.g. hypochlorite) bleaches. Perborate (e.g., mono- or tetra-hydrate sodium salts) and percarbonate bleaches can be used herein.

Another category of bleaching agent that can be used without restriction encompasses percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxy-dodecanedioic acid. Such bleaching agents are disclosed in U.S. Pat. No. 4,483,781, Hartman, issued Nov. 20, 1984. U.S. patent application Ser. No. 740,446, Burns et al, filed Jun. 3, 1985, European Patent Application 0,133,354, Banks et al, published Feb. 20, 1985, and U.S. Pat. No. 4,412,934. Chung et al, issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Peroxygen bleaching agents can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONE, manufactured commercially by DuPont) can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources such as FMC, Solvay and Tokai Denka.

Mixtures of bleaching agents can also be used.

Peroxygen bleaching agents, the perborates, the percarbonates, etc., are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915,854, issued Apr. 10, 1990 to Mao et al, and U.S. Pat. No. 4,412,934. The nonanoyloxybenzene sulfonate (NOBS) and tetraacetyl ethylene diamine (TAED) activators are typical, and mixtures thereof can also be used. See also U.S. Pat. No. 4,634,551 for other typical bleaches and activators useful herein.

Highly preferred amido-derived bleach activators are those of the formulae:

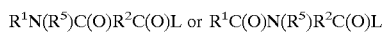

wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. A leaving group is any group that is displaced from the bleach activator as a consequence of the nucleophilic attack on the bleach activator by the perhydrolysis anion. A preferred leaving group is phenyl sulfonate.

Preferred examples of bleach activators of the above formulae include (6-octanamido-caproyl) oxybenzenesulfonate, (6-nonanamidocaproyl) oxybenzenesulfonate, (6-decanamido-caproyl) oxybenzenesulfonate, and mixtures thereof as described in U.S. Pat. No. 4,634,551, incorporated herein by reference.

Another class of bleach activators comprises the benzoxazin-type activators disclosed by Hodge et al in U.S. Pat. No. 4,966,723, issued Oct. 30, 1990, incorporated herein by reference. A highly preferred activator of the benzoxazin-type is:

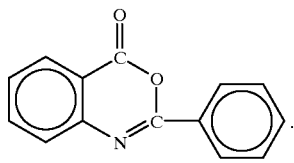

Still another class of preferred bleach activators includes the acyl lactam activators, especially acyl caprolactams and acyl valerolactams of the formulae:

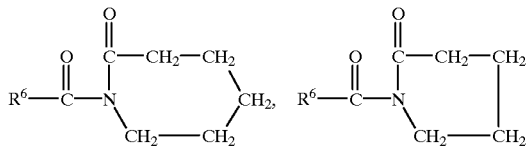

wherein $R^6$ is H or an alkyl, aryl, alkoxyaryl, or alkaryl group containing from 1 to about 12 carbon atoms. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, incorporated herein by reference, which discloses acyl caprolactams, including benzoyl caprolactam, adsorbed into sodium perborate.

As a practical matter, and not by way of limitation, the compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 500 ppm, of the catalyst species in the laundry liquor.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. See U.S. Pat. No. 4,033,718, issued Jul. 5, 1977 to Holcombe et al. If used, detergent compositions will typically contain from about 0.025% to about 1.25%, by weight, of such bleaches, especially sulfonate zinc phthalocyanine.

Buffers

Buffers can be included in the formulations herein for a variety of purposes. One such purpose is to adjust the cleaning surface pH to optimize the hard surface cleaner composition effectiveness relative to a particular type of soil or stain. Buffers may be included to stabilize the adjunct ingredients with respect to extended shelf life or for the purpose of maintaining compatibility between various aesthetic ingredients. The hard surface cleaner of the present invention optionally contains buffers to adjust the pH in a range from about 7 to about 13, preferably from about 8 to about 13, more preferably from about 10 to about 11. Non-limiting examples of such suitable buffers are potassium carbonate, sodium carbonate, and sodium bicarbonate, however, the formulator is not restricted to these examples or combinations thereof.

Adjunct Materials

The compositions herein can optionally include one or more other detergent adjunct materials or other materials for assisting or enhancing cleaning performance, treatment of the surface to be cleaned, or to modify the aesthetics of the composition (e.g., perfumes, colorants, dyes, etc.). The following are illustrative examples of such adjunct materials but are not meant to be exclusive or limiting in scope.

Chelating Agents

The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions Inert Salts The inert salts (filler salts) used in the compositions of the present invention can be any water-soluble inorganic or organic salt or mixtures of such salts which do not destabilize the surfactant. For the purposed of the present invention, "water-soluble" means having a solubility in water of at least 1 gram per 100 grams of water at 20° C. Examples of suitable salts include various alkali metal and/or alkali earth metal sulfate, chlorides, borates, bromides, fluorides, phosphates, carbonates, bicarbonates, citrates, acetates, lactates, etc.

Specific examples of suitable salts include sodium sulfate, sodium chloride, potassium chloride, sodium carbonate, potassium sulfate, lithium chloride, lithium sulfate, tripotassium phosphate, sodium borate, potassium bromide, potassium fluoride, sodium bicarbonate, magnesium sulfate, magnesium chloride, sodium citrate, sodium acetate, magnesium lactate, sodium fluoride. The preferred salts are inorganic salts preferably the alkali metal sulfates and chlorides. Particularly preferred salts, because of their low cost are sodium sulfate and sodium chloride. The salts are present in the compositions at levels of from 0% to 40%, preferably 10% to 20%.

Abrasives

An essential component of many solid or viscous semi-solid hard surface cleaning compositions is the abrasive material added to facilitate the action of scouring. Abrasive scouring cleansers provide a convenient and useful means for carrying out the sanitizing of porcelain and tile surfaces, especially tubs, showers and toilet bowls. The particulate abrasive material within such compositions serves to abrade and loosen soil adhering to hard surfaces and further serves to create more intimate contact between hard surface stain and the surfactant and/or bleaching agents also present in the cleansing compositions.

Abrasive cleaners have traditionally contained water-insoluble, relatively hard, particulate mineral material as the abrasive agent. The most common such abrasive agent is finely divided silica sand having particle size varying between about 1 and 300 microns and specific gravity of about 2.1 or higher. While such material is generally very effective in scouring soil and stains from the surfaces being treated, abrasive material of this type tends to be difficult to rinse away from the toilet bowl, shower or bathtub surface.

In the case where moderate or highly water soluble abrasive material is required (i.e. sodium carbonate) imidodisulfate can be used as the sole abrasive or otherwise added in part.

It has been discovered that abrasive compositions of this desired type can be realized by utilizing a particular type of expanded perlite abrasive in combination with the surfactants, filler material, and other optional scouring material ingredients listed herein. The abrasive materials suitable to the present invention are those contained in U.S. Pat. No. 4,051,056, Hartman, issued Sep. 27, 1977 and included herein by reference.

Perfumes

Perfumes are an important ingredient especially for the liquid composition embodiment. Perfume is usually used at levels of from 0% to 5%. In U.S. Pat. No. 4,246,129, Kacher, issued Jan. 20, 1981 (incorporated herein by reference), certain perfume materials are disclosed which perform the added function reducing the solubility of anionic sulfonate and sulfate surfactants.

Dyes

Dyes may be include at levels of from abut 0.5% to 12%, preferably 1.5% to 5%. Solids and viscous semi-solids can be made with 1.5% dye and no perfume. Examples of suitable dyes are Alizarine Light Blue B (C.I. 63010), Carta Blue VP (C.I. 24401), Acid Green 2G (C.I. 42085), Astrogen Green D (C.I. 42040), Supranol Cyanine 7B (C.I. 42675, Maxilon Blue 3RL (C.I. Basic Blue 80), Drimarine Blue Z-RL (C.I. Reactive Blue 18), Alizarine Light Blue H-RL (C.I. Acid Blue 182), FD&C Blue No. 1 and FD&C Green No. 3. (See the patents of Kitko, U.S. Pat. No. 4,248,827 issued Feb. 3, 1981 and U.S. Pat. No. 4,200,606, issued Apr. 29, 1980, both incorporated herein by reference.) C.I. refers to Color Index.

Optional Adjuncts Ingredients

As a preferred embodiment, the conventional adjunct ingredients employed herein can be selected from typical components such as enzymes (compatible with the applicable with other adjunct ingredients), especially proteases, lipases, cellulases, color speckles, suds boosters, suds supressors, anti-tarnish and/or anti-corrosion agents, soil-suspending agents, germicides, alkalinity sources, hydrotropes, anti-oxidants, enzyme stabilizing agents, solvents, clay soil chelating agents will generally comprise from about 0.1% to about 10% by weight of the detergent compositions herein. More preferably, if utilized. the chelating agents will comprise from about 0.1% to about 3.0% by weight of such composition removal/anti-redeposition agents, polymeric dispersing agents, dye transfer inhibiting agents, including polyamine N-oxides such as polyvinylpyrrolidone and copolymers of N-vinyl imidazole and N-vinyl pyrrolidone, etc.

EXAMPLE 1

Preparation of Dilithium Naphthalocyanine

To a refluxing solution of 2,3-dicyanonaphthalene (10 g, 56.1 mmole) in anhydrous 1-butanol (300 mL) is added lithium shot (1.56 g, 224.5 mmole). The solution is refluxed 6 hours under argon, diluted with 500 mL methanol and allowed to crystallize in the cold at about 0° C. for 18 hours. The resulting green solid is recovered by filtration, dried in vacuo at 80° C. and used without further purification.

The above procedure is suitable for preparing 1,4,8,11, 15,18,22,25-octabutoxy-29,31 -dilithium phthalocyanine from 3,6-dibutoxyphthalonitrile; 2,3,9,10,16,17,23,24-octachloro-29,31-dilithium phthalocyanine from 4,5-dichlorophthalonitrile; and tetrabutoxy-29,31-dilithium phthalcyanine from 3-butoxyphthalonitrile.

EXAMPLE 2

Preparation of Naphthalocyanine

To a solution of dilithium naphthalocyanine (2 g, 2.75 mmole) in DMF (200 ml) is added 1N HCl (10 mL). The solution is stirred at room temperature of approximately 1 hour. The solution is then diluted with 200 mL of water over a period of about 30 minutes. The green solid which results is collected by filtration and dried in vacuo at 100° C. and used without further purification.

The above procedure is suitable for preparing 1,4,8,11,15,18,22,25-octabutoxy-29H,31H-phthalocyanine; 2,3,9,10,16,17,23,24-octachloro-29H,31H-phthalocyanine; and tetrabutoxy-29H,31H-phthalcyanine.

EXAMPLE 3
Preparation of Tin(IV) Naphthalocyanine Dichloride

A mixture of naphthalocyanine (0.2 g, 0.28 mmole), tin tetrachloride pentahydrate (0.456 g, 1.3 mmole) in DMF is refluxed for one hour under argon then allowed to cool. The green solid that results is filtered off, dired in vacuo, and used without further purification.

The above procedure is suitable for preparing 1,4,8,11,15,18,22,25-octabutoxy tin(IV) phthalocyanine dichloride; 2,3,9,10,16,17,23,24-octachloro tin(IV) phthalocanine dichloride; and tetrabutoxy tin(IV) phthalcyanine dichloride.

EXAMPLE 4
Preparation of Germanium(lV) Naphthalocyanine Dichloride

To a refluxing solution of naphthalocyanine (0.20 g, 0.28 mmole), germanium tetrachloride (0.15 mL) in anhydrous DMF (20 mL) under argon, is added in portions over a period of 5 hours additional germanium tetrachloride (0.25 mL). The solution is cooled, diluted with dichloromethane 940 mL), extracted twice with 30 mL portions of 10% hydrochloric acid, then three times with 30 mL portions of distilled water, died over MgSO$_4$, filtered and concentrated to yield a green solid that is used without further purification.

The above procedure is suitable for preparing 1,4,8,11,15,18,22,25-octabutoxy germanium(IV) phthalocyanine dichloride; 2,3,9,10,16,17,23,24-octachloro germanium(IV) phthalocyanine dichloride; and tetrabutoxy germanium(IV) phthalcyanine dichloride.

EXAMPLE 5
Preparation of 1,4,8,11,15,18,22,25-octabutoxy Platinum (IV) Dichloride To a refluxing solution of 1,4,8,11,15,18,22,25-Octabutoxyphthalocyanine (0.20 g, 0.18 mmole), Platinum Tetrachloride (0.15 ml) in 20 ml anhydrous N,N-Dimethylformamide under argon over a five hour period is added in five portions Platinum Tetrachloride (0.25 ml). The solution is cooled, diluted with 40 ml Dichloromethane, extracted 2×30 ml 10% hydrochloric acid, 3×30 ml distilled water, dried over anhydrous Magnesium Sulfate and stripped of solvent yielding a green solid which is used without further purification.

EXAMPLE 6
Preparation of 1,4,8,11,15,18,22,25-octabutoxy Germanium (IV) Phthalocyaninedi-(poly(ethylene glycol 350) Methyl Ether)

A mixture of 1,4,8,11,15,18,22,25-octabutoxy germanium (IV) phthalocyanine dihydroxide (1.0 g, 0.81 mmole), poly (ethylene glycol 350) methyl ether (22.68 g, 64.8 mmole) and xylene (175 mL) is slowly heated to reflux under argon over a period of 3 hours. The reaction flask is fitted with a Dean-Stark trap and the water is removed by azeotropic distillation. After 48 hours the reaction is cooled, the solvent removed in vacuo and the crude product is used without further purification.

The above procedure is suitable for use in preparing 1,4,8,11,15,18,22,25-octabutoxy germanium(IV) phthalocyanine-di-(glycerol-di-(diethylene glycol methyl ether)); 1,4,8,11,15,18,22,25-octabutoxy germanium(IV) phthalcyanine-di-(Neodol 23-6.5); tetrabutoxy tin(IV) phthalcyanine-di-(poly(ethylene glycol 350) methyl ether); tetrabutoxy tin(IV) phthalcyanine-di-(glycerol-di-(diethylene glycol methyl ether)); and tetrabutoxy tin(IV) phthalcyanine-di-(Neodol 23–6.5).

EXAMPLE 7
Preparation of 1,4,8,11,15,18,22,25-octabutoxy Germanium (IV) Phthalocyanine-di-(Triethanol Amine Dimethyl Sulfate Quat.)

A mixture of 1,4,8,11,15,18,22,25-octabutoxy germanium (IV) phthalocyanine dihydroxide (0.5 g, 0.405 mmole), anhydrous triethanolamine (10 g, 67.04 mmole) and xylene (175 mL) is slowly heated to reflux over a period of 1.5 hours. The reaction flask is fitted with a Dean-Stark trap and the water is removed by azeotropic distillation. After 2 hours the solution is cooled, and the solvent is removed in vacuo. The resulting oil is dissolved in 50 mL DMF and slowly added to 800 mL of water over 0.5 hour. The blue solid which results is collected by filtration and dried under vacuum at 80° C. This solid product is added to a dioxane (100 mL) which contains dimethylsulfate (0.15 g, 1.215 mmole). The resulting blue solid is collected by filtration, dried and used without further purification.

The above procedure is suitable for use in preparing tetrabutoxy tin(IV) phthalcyanine-di-(triethanolamine dimethyl sulfate quat).

The cleaning compositions provided in accordance with this invention may be in the form of granules, liquids, bars, and the like, and typically are formulated to provide an in-use pH in the range of 9 to 11, however in the case of non-aqueous or low aqueous compositions the pH ranges may vary outside this range. Various carriers such as sodium sulfate, water, water-ethanol, BPP, MPP, EPP, PPP, sodium carbonate, and the like, may be used routinely to formulate the finished products. Granules may be produced by spray-drying or by agglomeration, using known techniques, to provide products in the density range of 350–950 g/l. Bars may be formulated using conventional extrusion techniques. The photobleach-chelant may be pre-formed, if desired. The compositions may also contain conventional perfumes, bactericides, hydrotropes and the like. In the case of non-aqueous or low aqueous compositions, the cleaning compositions may be applied to an article which is used to deliver the compositions of the present invention to a fabric or to a hard surface. Non-limiting examples of compositions according to this invention are as follows:

EXAMPLES 8-11

| | Weight % | | | |
|---|---|---|---|---|
| Ingredients | 8 | 9 | 10 | 11 |
| Sodium linear alkylbenzene sulfonate | 15 | 30 | 20 | 25 |
| NEODOL | 1 | 1 | 1 | 1 |
| Alkyl dimethyl ammonium chloride | 0.5 | 1 | 0.5 | 0.7 |
| Sodium tripolyphosphate | 15 | 35 | 22 | 28 |
| Sodium carbonate | 10 | 10 | 15 | 15 |
| SOKALAN | 2 | 2 | 2 | 2 |
| Carboxymethylcellulose | 1 | 1 | 1 | 1 |

-continued

| Ingredients | Weight % | | | |
|---|---|---|---|---|
| | 8 | 9 | 10 | 11 |
| Tinopal CBS-X | 0.1 | 0.1 | 0.1 | 0.1 |
| Soil release agent[1] | 0.2 | 0.2 | 0.3 | 0.3 |
| Savinase 6.0 T | 0.3 | 0.6 | 0.5 | 0.6 |
| Ban 300 T | 0.2 | 0.5 | 0.5 | 0.6 |
| Lipolase 100 T | 0.1 | 0.2 | 0.2 | 0.3 |
| CAREZYME 5 T | 0.1 | 0.2 | 0.2 | 0.3 |
| Sodium perborate | — | — | 3 | 5 |
| Nonanoyloxybenzenesulfonate | — | — | 2 | 3 |
| Photobleach[2](ppm) | 0.005 | 0.01 | — | — |
| Photobleach[3](ppm) | — | — | 0.008 | 0.01 |
| Minors/fillers | balance | balance | balance | balance |

[1]Soil release polymer according to U.S. Pat. No. 4,968,451 Scheibel et al.
[2]Photobleach germanium(IV)octabutoxyphthalocyanine poly(ethylene glycol 350) according to Example 6
[3]Photobleach tin(IV)octabutoxyphthalocyanine poly(ethylene glycol 350) according to Example 6

EXAMPLES 12-15

| Ingredients | Weight % | | | |
|---|---|---|---|---|
| | 12 | 13 | 14 | 15 |
| $C_{12}$—$C_{14}$ alkyl sulfate | 6 | 6 | 8 | 7 |
| $C_{12}$—$C_{14}$ alkyl ethoxylate (EO 4.2) | 11 | 12 | 10 | 5 |
| Zeolite | 38 | 35 | 30 | 10 |
| Trisodium citrate | — | — | — | 2 |
| SKS-6 silicate builder | — | — | — | 10 |
| Acrylate/maleate copolymer | — | — | — | 4 |
| Sodium carbonate | 9 | 10 | 4 | 5 |
| EDTMP[1] | 0.2 | — | 0.3 | — |
| Ethylenediamine disuccinate | — | — | — | 0.4 |
| Sodium percarbonate | 8 | — | 10 | 25 |
| Nonanolyoxybenzene sulfonate | — | — | 3 | — |
| Tetraacetylethylenediamine | 7 | — | — | — |
| Savinase (4.0 KNPU/g) | 2 | 1.5 | 2 | 1.5 |
| Lipolase (100,000 LU/g) | 0.2 | 0.5 | 0.5 | — |
| Soap | 1 | — | — | — |
| Suds suppressor | 2 | 2 | 2 | 2 |
| Soil release agent[2] | 0.5 | — | 0.5 | — |
| Soil release agent[3] | 0.5 | 0.5 | — | 0.5 |
| Dispersent[4] | — | 2.5 | — | — |
| Photobleach[5](ppm) | 0.005 | 0.01 | — | — |
| Photobleach[6](ppm) | — | — | 0.008 | 0.01 |
| Minors/fillers | balance | balance | balance | balance |

[1]Ethylenediamine tetramethylenephosphonate
[2]Soil release polymer according to U.S. Pat. No. 5,415,807, Gosselink et al. issued May 16, 1995.
[3]Soil release polymer according to U.S. Pat. No. 4,702,857, Gosselink issued October 27, 1987.
[4]Hydrophobic soil dispersant according to U.S. Pat. No. 5,565,145, Watson et al. issued October 15, 1996.
[5]Photobleach germanium(IV) octabutoxyphthalocyanine according to Example 7.
[6]Photobleach tin(IV) tetrabutoxyphthalocyanine according to Example 7.

EXAMPLE 16

| Ingredients | Weight % |
|---|---|
| $C_{12}$ Linear alkyl benzene sulphonate | 30 |
| Phosphate (as sodium tripolyphosphate) | 7 |
| Sodium carbonate | 15 |
| Sodium pyrophosphate | 7 |
| Coconut monoethanolamide | 2 |
| Zeolite A | 5 |

-continued

| Ingredients | Weight % |
|---|---|
| Carboxymethylcellulose | 0.2 |
| Polyacrylate (m.w. 1400) | 0.2 |
| Sodium percarbonate | 15 |
| Protease | 0.3 |
| $CaSO_4$ | 1 |
| $MgSO_4$ | 1 |
| Photobleach[1](ppm) | 0.01 |
| Minors/fillers | balance |

[1]Photobleach germanium(IV) octabutoxyphthalocyanine-di-(Neodol 23-6.5)

Low Aqueous Cleaning Composition

EXAMPLE 17

| Ingredients | Weight % |
|---|---|
| Photobleach[1] | 0.005–1.5 |
| BPP[2] | 5–25 |
| 1,2-octanediol | 0.1–70 |
| Magnesium alkylethoxy (E1) sulfate | 0.01–0.8 |
| Magnesium alkylethoxy (E6.5) sulfate | 0.01–0.8 |
| $C_{12}$ dimethylamine oxide | 0.01–0.8 |
| PEMULEN[3] | 0.05–0.2 |
| Perfume | 0.01–1.5 |
| Water | balance |

[1]Photobleach germanium(IV) octabutoxyphthalocyanine di[glycerol-di-(diethylene glycol methyl ether)].
[2]Other co-solvents which can be used herein together with the BPP, MPP, EPP and PPP primary solvents include various glycol ethers, including materials marketed under trademarks such as Carbitol, methyl Carbitol, butyl Carbitol, propyl Carbitol, hexyl Cellosolve, and the like. If desired, and having due regard for safety and odor for in-home use, various conventional chlorinated and hydrocarbon dry cleaning solvents may also be used. Included among these are 1,2-dichloroethane, trichloroethylene, isoparaffins, and mixtures thereof.
[3]As disclosed in U.S. Pat. Nos. 4,758,641 and 5,004,557, such polyacrylates include homopolymers which may be crosslinked to varying degrees, as well as non-crosslinked. Preferred herein are homopolymers having a molecular weight in the range of from about 100,000 to about 10,000,000, preferably 2000,000 to 5,000,000.

For the materials disclosed in Example 29, excellent cleaning performance is secured using any non-immersion processes and articles to provide from about 5 g to about 50 g of the cleaning compositions per kilogram of fabric being cleaned. Use of the polyacrylate emulsifier at the indicated low levels minimizes residues on the fabrics.

Fabrics are laundered using the foregoing compositions, typically at usage concentrations of from about 10 ppm to about 10,000 ppm. The fabrics are dried in the presence of light, preferably natural sunlight, to achieve improved photobleaching benefits.

What is claimed is:

1. A photochemical singlet oxygen generator having a Q-band maximum absorption wavelength of 660 nanometers or greater, having the formula:

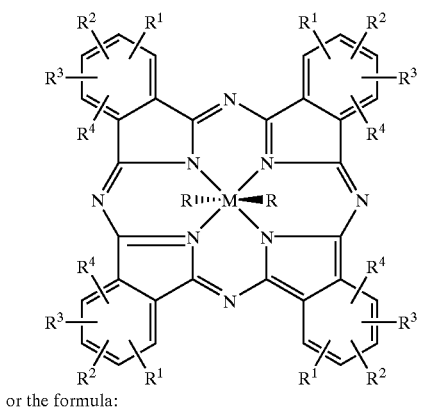

or the formula:

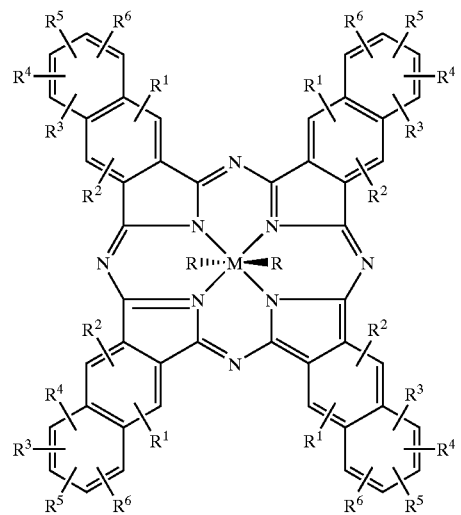

wherein M is a photoactive metal or non-metal, said metal or non-metal selected from the group consisting of Sn, Pt, Pd, Pb and mixtures thereof; $R^1$, $R^2$, $R^3$, $R^4$, $R^5$, and $R^6$ units are each independently selected from the group consisting of:

a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;
h) branched alkoxy having the formula:

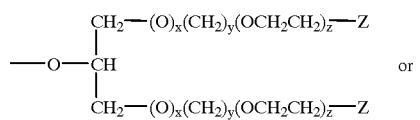

or

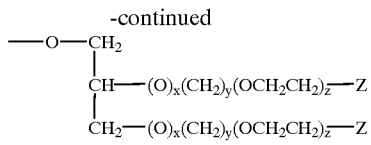

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;

i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) an ester of the formula —$CO_2R^9$ wherein $R^9$ is
 i) $C_1$–$C_{22}$ alkyl, $C_3$–$C_{22}$ branched alkyl, $C_2$–$Cs_2$ alkenyl, $C_3$–$C_{22}$ branched alkenyl, or mixtures thereof;
 ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
 iii) polyhydroxyl substituted $C_3$–$C_{22}$ alkylene;
 iv) $C_3$–$C_{22}$ glycol;
 v) $C_1$–$C_{22}$ alkoxy;
 vi) $C_3$–$C_{22}$ branched alkoxy;
 vii) substituted aryl, unsubstituted aryl, or mixtures thereof;
 viii) substituted alkylenearyl, unsubstituted alkylenearyl, or mixtures thereof;
 ix) substituted aryloxy, unsubstituted aryloxy, or mixtures thereof;
 x) substituted oxyalkylenearyl, unsubstituted oxyalkylenearyl, or mixtures thereof;
 xi) substituted alkyleneoxyaryl, unsubstituted alkyleneoxyaryl, or mixtures thereof;
p) an alkyleneamino unit of the formula:

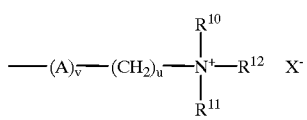

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof; $R^{12}$ is:
 i) hydrogen;
 ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

A is nitrogen or oxygen; X is chlorine, bromine, iodine, or other water soluble anion, v is 0 or 1, u is from 0 to 22;

q) an amino unit of the formula:

—NR$^{17}$R$^{18}$ wherein R$^{17}$ and R$^{18}$ are C$_1$–C$_{22}$ alkyl, C$_3$–C$_{22}$ branched alkyl, C$_2$–C$_{22}$ alkenyl, C$_3$–C$_{22}$ branched alkenyl, or mixtures thereof;

r) an alkylethyleneoxy unit of the formula:

$$-(A)_v-(CH_2)_y(OCH_2CH_2)_xZ$$

wherein Z is:
i) hydrogen;
ii) hydroxyl;
iii) —CO$_2$H;
iv) —SO$_3^-$M$^+$;
v) —OSO$_3^-$M$^+$;
vi) C$_1$–C$_6$ alkoxy;
vii) substituted aryl, unsubstituted aryl, or mixtures thereof;
viii) substituted aryloxy, unsubstituted aryloxy, or mixtures thereof;
ix) alkyleneanino; or mixtures thereof;

A is nitrogen or oxygen, M is a water soluble cation, v is 0 or 1, x is from 0 to 100, y is from 0 to 12;

s) substituted siloxy of the formula:

$$-OSiR^{19}R^{20}R^{21}$$

wherein each R$^{19}$, R$^{20}$, and R$^{21}$ is independently
i) C$_1$–C$_{22}$ alkyl, C$_3$–C$_{22}$ branched alkyl, C$_2$–C$_{22}$ alkenyl, C$_3$–C$_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

$$-(A)_v-(CH_2)_y(OCH_2CH_2)_xZ;$$

wherein Z is:
a) hydrogen;
b) hydroxyl;
c) —CO$_2$H;
d) —SO$_3^-$M$^+$;
e) —OSO$_3^-$M$^+$;
f) C$_1$–C$_6$ alkoxy;
g) substituted aryl, unsubstituted aryl, or mixtures thereof;
h) substituted aryloxy, unsubstituted aryloxy, or mixtures thereof;
i) alkyleneamino; or mixtures thereof;

A is nitrogen or oxygen, M is a water soluble cation, v is 0 or 1, x is from 0 to 100, y is from 0 to 12;

and mixtures thereof axial R units wherein each R is independently selected from the group consisting of:
a) hydrogen;
b) halogen;
c) hydroxy;
d) C$_1$–C$_{22}$ alkyl, C$_3$–C$_{22}$ branched alkyl, C$_2$–C$_{22}$ alkenyl, C$_3$–C$_{22}$ branched alkenyl, or mixtures thereof;

e) halogen substituted C$_1$–C$_{22}$ alkyl, C$_3$–C$_{22}$ branched alkyl, C$_2$–C$_{22}$ alkenyl, C$_3$–C$_{22}$ branched alkenyl, or mixtures thereof;

f) polyhydroxyl substituted C$_3$–C$_{22}$ alkyl;

g) C$_1$–C$_{22}$ alkoxy;

h) branched alkoxy having the formula:

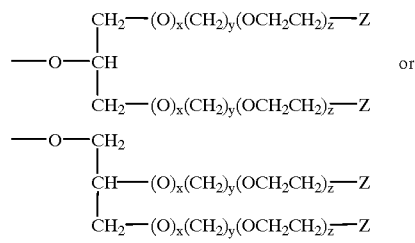

wherein Z is hydrogen, hydroxyl, C$_1$–C$_{30}$ alkyl, C$_1$–C$_{30}$ alkoxy, —CO$_2$H, —OCH$_2$CO$_2$H, —SO$_3^-$M$^+$, —OSO$_3^-$M$^+$, —PO$_3^{2-}$M, —OPO$_3^{2-}$M, or mixtures thereof; M is a water soluble cation in sufficient amount to satisfy charge balance; x is 0 or 1, each y independently has the value from 0 to 6, each z independently has the value from 0 to 100;

i) substituted aryl, unsubstituted aryl, or mixtures thereof;

j) substituted alkylenearyl, unsubstituted alkylenearyl, or mixtures thereof;

k) substituted aryloxy, unsubstituted aryloxy, or mixtures thereof;

l) substituted oxyalkylenearyl, unsubstituted oxyalkylenearyl, or mixtures thereof;

m) substituted alkyleneoxyaryl, unsubstituted alkyleneoxyaryl, or mixtures thereof;

n) C$_1$–C$_{22}$ thioalkyl, C$_3$–C$_{22}$ branched thioalkyl, or mixtures thereof;

o) a carboxylate of the formula:

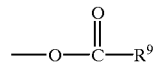

wherein R$^9$ is:
i) C$_1$–C$_{22}$ alkyl, C$_3$–C$_{22}$ branched alkyl, C$_2$–C$_{22}$ alkenyl, C$_3$–C$_{22}$ branched alkenyl, or mixtures thereof;
ii) halogen substituted C$_1$–C$_{22}$ alkyl, C$_3$–C$_{22}$ branched alkyl, C$_2$–C$_{22}$ alkenyl, C$_3$–C$_{22}$ branched alkenyl, or mixtures thereof;
iii) polyhydroxyl substituted C$_3$–C$_{22}$ alkylene;
iv) C$_3$–C$_{22}$ glycol;
v) C$_1$–C$_{22}$ alkoxy;
vi) C$_3$–C$_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;

x) substituted oxyalkylenearyl, unsubstituted oxyalkylenearyl, or mixtures thereof;
xi) substituted alkyleneoxyaryl, unsubstituted alkyleneoxyaryl, or mixtures thereof;
p) an alkyleneamino unit of the formula:

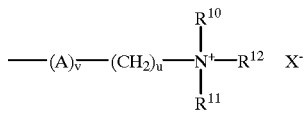

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof; $R^{12}$ is:
i) hydrogen;
ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
A is nitrogen or oxygen; X is chlorine, bromine, iodine, or other water soluble anion, v is 0 or 1, u is from 0 to 22;
q) an amino unit of the formula:

wherein $R^{17}$ and $R^{18}$ are $C_1$–$C_{22}$ alkyl, $C_3$–$C_{22}$ branched alkyl, $C_2$–$C_{12}$ alkenyl, $C_3$–$C_{22}$ branched alkenyl, or mixtures thereof;
r) an alkylethyleneoxy unit of the formula:

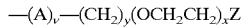

wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;
A is nitrogen or oxygen, M is a water soluble cation, v is 0 or 1, x is from 0 to 100, y is from 0 to 12;
s) substituted siloxy of the formula:

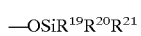

wherein each $R^{19}$, $R^{20}$, and $R^{21}$ is independently
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

wherein Z is:
a) hydrogen;
b) hydroxyl;
c) —$CO_2H$;
d) —$SO_3^-M^+$;
e) —$OSO_3^-M^+$;
f) $C_1$–$C_6$ alkoxy;
g) substituted aryl, unsubstituted aryl, or mixtures thereof;
h) substituted aryloxy, unsubstituted aryloxy, or mixtures thereof;
i) alkyleneamino; or mixtures thereof;
A is nitrogen or oxygen, M is a water soluble cation, v is 0 or 1, x is from 0 to 100, y is from 0 to 12; and mixtures thereof.

2. A method for cleaning a hard surface comprising contacting a hard surface in need of cleaning with an aqueous cleaning composition comprising at least 0.001 ppm photosensitizing compound according to claim 1 and exposing the hard surface to a source of light having a minimal wavelength range from about 300 to about 1200 nanometers.

3. A method for cleaning a stained fabric with a cleaning material comprising a low aqueous cleaning composition comprising contacting a stained fabric in need of stain removal with a low aqueous cleaning solution comprising less than 50% water and at least 0.001 ppm of the photosensitizing compound according to claim 1 followed by exposing the surface of the treated fabric to a source of light having a minimal wavelength range from about 300 to about 1200 nanometers.

4. A method for cleaning a hard surface with a low aqueous cleaning composition comprising contacting a hard surface in need of cleaning with a low aqueous cleaning composition comprising less than 50% water and at least 0.001 ppm of the photosensitizing compound according to claim 1 and exposing the hard surface to a source of light having a minimal wavelength range from about 300 to about 1200 nanometers.

5. A bleaching composition comprising:
a) at least about 0.01% of a non-hypohalite bleach;
b) at least about 0.001 ppm of a photosensitizing compound having a Q-band maximum absorption wavelength of 660 nanometers or greater according to claim 1; and
c) the balance carriers and adjunct ingredients.

6. A composition according to claim 5 wherein the non-hypohalite bleach is a selected from the group consisting of percarboxylic acids, peroxides, percarbonates, perborates, and mixtures thereof.

7. A laundry or cleaning composition comprising:
A) from about 0.1% by weight, of a detersive surfactant, said detersive surfactant is selected from the group consisting of anionic, cationic, nonionic, zwitterionic, ampholytic surfactants, and mixtures thereof;
B) from about 0.001 ppm of a photosensitizing compound having a Q-band maximum absorption wavelength of 660 nanometers or greater having the formula:

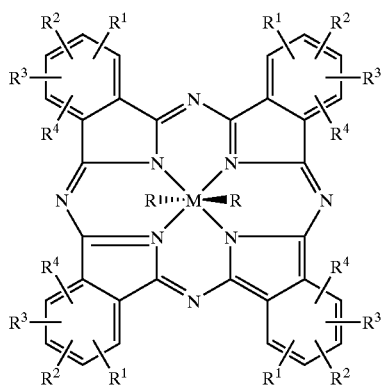

or having the formula:

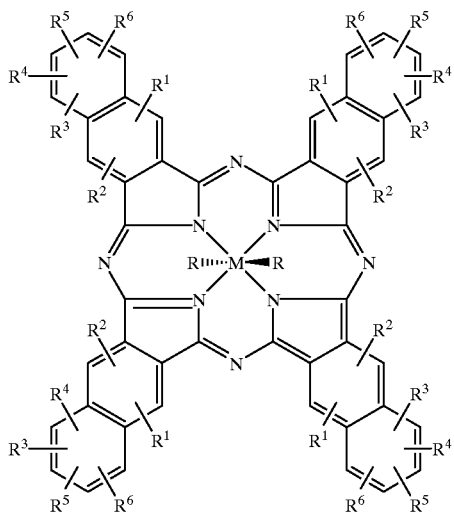

wherein M is a photoactive metal or non-metal, said metal or non-metal selected from the group consisting of Sn, Pt, Pd, P and mixtures thereof; $R^1$, $R^2$, $R^3$, $R^4$, $R^5$, and $R^6$ units are each independently selected from the group consisting of:

a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;
h) branched alkoxy having the formula:

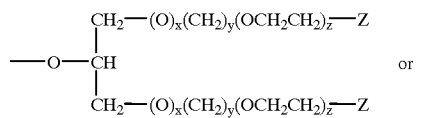 or

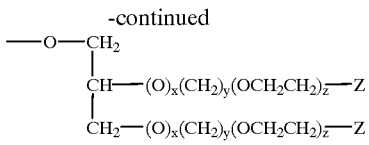

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;

i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkylencoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) an ester of the formula —$CO_2R^9$ wherein $R^9$ is
   i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
   ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
   iii) polyhydroxyl substituted $C_3$–$C_{22}$ alkylene;
   iv) $C_3$–$C_{22}$ glycol;
   v) $C_1$–$C_{22}$ alkoxy;
   vi) $C_3$–$C_{22}$ branched alkoxy;
   vii) substituted aryl, unsubstituted aryl, or mixtures thereof;
   viii) substituted alkylenearyl, unsubstituted alkylenearyl, or mixtures thereof;
   ix) substituted aryloxy, unsubstituted aryloxy, or mixtures thereof;
   x) substituted oxyalkylenearyl, unsubstituted oxyalkylenearyl, or mixtures thereof;
   xi) substituted alkyleneoxyaryl, unsubstituted alkyleneoxyaryl, or mixtures thereof;
p) an alkyleneamino unit of the formula:

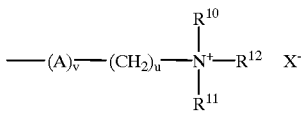

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof; $R^{12}$ is:
   i) hydrogen;
   ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
A is nitrogen or oxygen; X is chlorine, bromine, iodine, or other water soluble anion, v is 0 or 1, u is from 0 to 22;
q) an amino unit of the formula:

—$NR^{17}R^{18}$ wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) an alkylethyleneoxy unit of the formula:

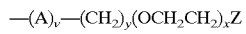

wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;
A is nitrogen or oxygen, M is a water soluble cation, v is 0 or 1, x is from 0, to 100, y is from 0 to 12;

s) substituted siloxy of the formula:

wherein each $R^{19}$, $R^{20}$, and $R^{21}$ is independently
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

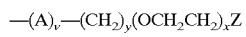

wherein Z is:
a) hydrogen;
b) hydroxyl;
c) —$CO_2H$;
d) —$SO_3^-M^+$;
e) —$OSO_3^-M^+$;
f) $C_1$–$C_6$ alkoxy;
g) substituted aryl, unsubstituted aryl, or mixtures thereof;
h) substituted aryloxy, unsubstituted aryloxy, or mixtures thereof;
i) alkyleneamino; or mixtures thereof;
A is nitrogen or oxygen, M is a water soluble cation, v is 0 or 1, x is from 0 to 100, y is from 0 to 12;

and mixtures thereof axial R units wherein each R is independently selected from the group consisting of:
a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;

h) branched alkoxy having the formula:

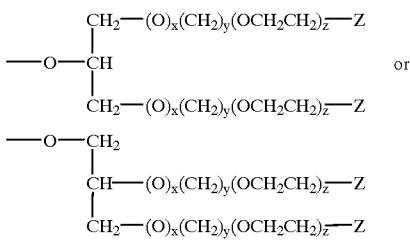

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, $PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;

i) substituted aryl, unsubstituted aryl, or mixtures thereof;

j) substituted alkylenearyl, unsubstituted alkylenearyl, or mixtures thereof;

k) substituted aryloxy, unsubstituted aryloxy, or mixtures thereof;

l) substituted oxyalkylenearyl, unsubstituted oxyalkylenearyl, or mixtures thereof;

m) substituted alkyleneoxyaryl, unsubstituted alkyleneoxyaryl, or mixtures thereof;

n) $C_1$–$C_{22}$ thioalkyl, $C_3$–$C_{22}$ branched thioalkyl, or mixtures thereof;

o) a carboxylate of the formula:

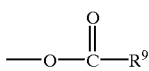

wherein $R^9$ is:
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
iii) polyhydroxyl substituted $C_3$–$C_{22}$ alkylene;
iv) $C_3$–$C_{22}$ glycol;
v) $C_1$–$C_{22}$ alkoxy;
vi) $C_3$–$C_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;
x) substituted oxyalkylenearyl, unsubstituted oxyalkylenearyl, or mixtures thereof;
xi) substituted alkyleneoxyaryl, unsubstituted alkyleneoxyaryl, or mixtures thereof;

p) an alkyleneamino unit of the formula:

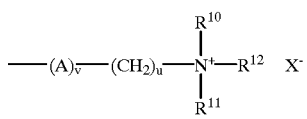

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof; $R^{12}$ is:
i) hydrogen;
ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

A is nitrogen or oxygen; X is chlorine, bromine, iodine, or other water soluble anion, v is 0 or 1, u is from 0 to 22;

q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) an alkylethyleneoxy unit of the formula:

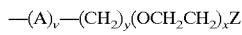

wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;

A is nitrogen or oxygen, M is a water soluble cation, v is 0 or 1, x is from 0 to 100, y is from 0 to 12;

s) substituted siloxy of the formula:

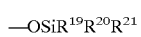

wherein each $R^{19}$, $R^{20}$, and $R^{21}$ is independently
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

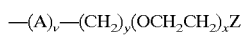

wherein Z is:
a) hydrogen;
b) hydroxyl;
c) —$CO_2H$;
d) —$SO_3^-M^+$;
e) —$OSO_3^-M^+$;
f) $C_1$–$C_6$ alkoxy;
g) substituted aryl, unsubstituted aryl, or mixtures thereof;

h) substituted aryloxy, unsubstituted aryloxy, or mixtures thereof;
i) alkyleneamino; or mixtures thereof;

A is nitrogen or oxygen, M is a water soluble cation, v is 0 or 1, x is from 0 to 100, y is from 0 to 12; and mixtures thereof; and C) the balance carriers and adjunct ingredients.

8. A composition according to claim 7 comprising from about 0.01 ppm to about 10000 ppm of said photosensitizing compound.

9. A composition according to claim 8 comprising from about 0.1 ppm to about 5000 ppm of said photosensitizing compound.

10. A composition according to claim 9 comprising from about 10 ppm to about 1000 ppm of said photosensitizing compound.

11. A composition according to claim 7 wherein the photosensitizing compound comprises $R^1$, $R^2$, $R^3$, $R^4$, $R^5$, and $R^6$ units independently selected from the group consisting of hydrogen, hydroxyl, halogen, $C_1$–$C_{22}$ thioalkyl, $C_3$–$C_{22}$ branched thioalkyl, $C_1$–$C_{22}$ alkoxy, $C_3$–$C_{22}$ branched alkoxy, aryloxy, an alkylethyleneoxy unit of the formula:

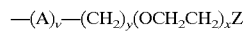

wherein Z comprises hydrogen, hydroxyl, —$CO_2H$, —$SO_3^-M^+$, —$OSO_3^-M^+$, $C_1$–$C_6$ alkoxy, substituted and unsubstituted aryl, substituted and unsubstituted aryloxy, alkyleneamino; and mixtures thereof, A comprises nitrogen or oxygen, M is a water soluble cation, v is 0 or 1, x is from 0 to 100, y is from 0 to 12.

12. A composition according to claim 2 wherein axial R units comprise:

a) alkylethyleneoxy units of the formula

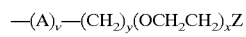

wherein Z comprises hydrogen, hydroxyl, —$CO_2H$, —$SO_3^-M^+$, —$OSO_3^-M^+$, $C_1$–$C_6$ alkoxy, substituted and unsubstituted aryl, substituted and unsubstituted aryloxy, alkyleneamino; A comprises nitrogen or oxygen, M is a water soluble cation, v is 0 or 1, x is from 0 to 100, y is from 0 to 12;

b) branched alkoxy having the formula

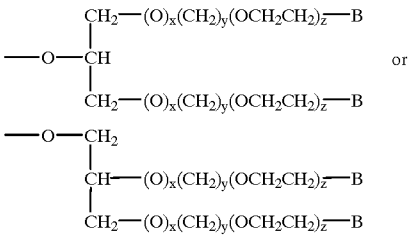

wherein B is hydrogen, hydroxyl, $C_1$–$C_{30}$ alkyl, $C_1$–$C_{30}$ alkoxy, —$CO_2H$, —$CH_2CO_2H$, —$SO_3^-M^+$, —$OSO_3^-M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, each z independently has the value from 0 to 100;

c) substituted siloxy of the formula

—OSiR$^7$R$^8$R$^9$ wherein each R$^7$, R$^8$, and R$^9$ is independently selected from the group consisting of C$_1$–C$_{22}$ alkyl, C$_3$–C$_{22}$ branched alkyl, C$_2$–C$_{22}$ alkenyl, C$_3$–C$_{22}$ branched alkenyl, substituted and unsubstituted aryl, substituted and unsubstituted aryloxy, an alkylethyleneoxy unit of the formula

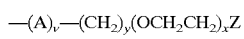
—(A)$_v$—(CH$_2$)$_y$(OCH$_2$CH$_2$)$_x$Z wherein Z comprises hydrogen, C$_1$–C$_{30}$ alkyl, hydroxyl, —CO$_2$H, —SO$_3$$^-$M$^+$, —OSO$_3$$^-$M$^+$, C$_1$–C$_6$ alkoxy, substituted and unsubstituted aryl, substituted and unsubstituted aryloxy, alkyleneamino, and mixtures thereof, A units comprise nitrogen or oxygen, M is a water soluble cation, v is 0 or 1, x is from 0 to 100, y is from 0 to 12.

13. A composition according to claim 12 wherein R is a branched alkoxy having the formula:

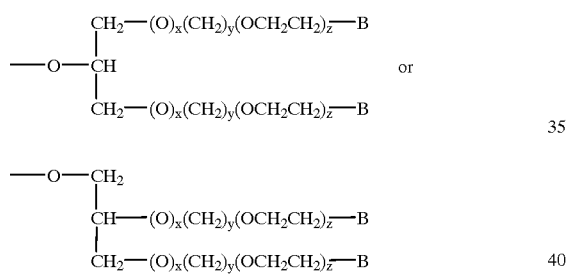

wherein B is hydrogen, hydroxyl, C$_1$–C$_{30}$ alkyl, C$_1$–C$_{30}$ alkoxy, —CO$_2$H, —CH$_2$CO$_2$H, —SO$_3$$^-$M$^+$, —OSO$_3$$^-$M$^+$, —PO$_3$$^{2-}$M, —OPO$_3$$^{2-}$M, and mixtures thereof; M is a water soluble cation in sufficient amount to satisfy charge balance; x is 0 or 1, each y independently has the value from 0 to 6, each z independently has the value from 0 to 100.

14. A composition according to claim 7 wherein the adjunct ingredients are members selected from the group consisting of buffers, builders, chelants, filler salts, soil release agents dispersants, enzymes, enzyme boosters, perfumes, thickeners, solvents, clays, bleaches, and mixtures thereof.

15. A laundry or cleaning composition comprising:

A) from about 0.1% by weight, of a detersive surfactant, said detersive surfactant is selected from the group consisting of anionic, cationic, nonionic, zwitterionic, ampholytic surfactants, and mixtures thereof;

B) from about 0.001 ppm of a photosensitizing compound having a Q-band maximum _ absorption wavelength of 660 nanometers or greater having the formula:

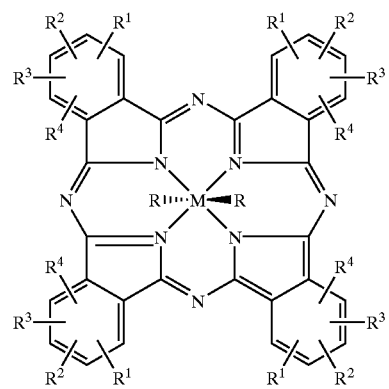

or having the formula:

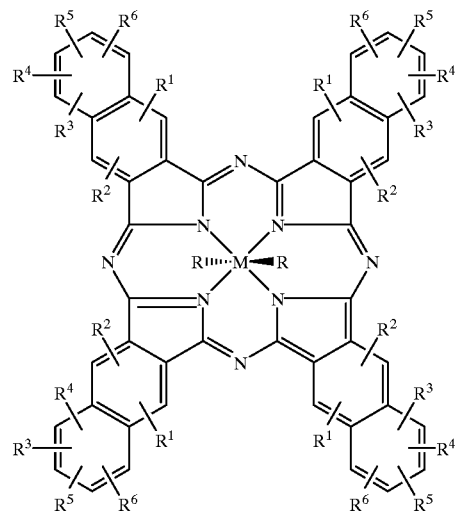

wherein M is a photoactive metal or non-metal selected from the group consisting of Sn, Pt, Pd, P and mixtures thereof;

R$^1$, R$^2$, R$^3$, R$^4$, R$^5$, and R$^6$ units are moieties that provide a positive $\Delta_{triplet}$ yield of at least 1 when said moiety replaces hydrogen;

wherein the R units are axial units, said R units independently selected from the group consisting of:

a) hydrogen;
b) halogen;
c) hydroxy;
d) C$_1$–C$_{22}$ alkyl, C$_3$–C$_{22}$ branched alkyl, C$_2$–C$_{22}$ alkenyl, C$_3$–C$_{22}$ branched alkenyl, or mixtures thereof;
e) halogen substituted C$_1$–C$_{22}$ alkyl, C$_3$–C$_{22}$ branched alkyl, C$_2$–C$_{22}$ alkenyl, C$_3$–C$_{22}$ branched alkenyl, or mixtures thereof;
f) polyhydroxyl substituted C$_3$–C$_{22}$ alkyl;
g) C$_1$–C$_{22}$ alkoxy;
h) branched alkoxy having the formula:

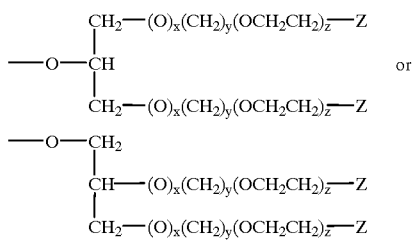

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;
i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) a carboxylate of the formula:

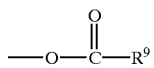

wherein $R^9$ is:
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
iii) polyhydroxyl substituted $C_3$–$C_{22}$ alkylene;
iv) $C_3$–$C_{22}$ glycol;
v) $C_1$–$C_{22}$ alkoxy;
vi) $C_3$–$C_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;
x) substituted oxyalkylenearyl, unsubstituted oxyalkylenearyl, or mixtures thereof;
xi) substituted alkyleneoxyaryl, unsubstituted alkyleneoxyaryl, or mixtures thereof;
p) an alkyleneamino unit of the formula:

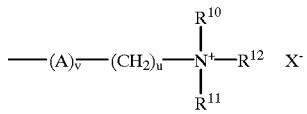

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof; $R^{12}$ is:
i) hydrogen;
ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
A is nitrogen or oxygen; X is chlorine, bromine, iodine, or other water soluble anion, v is 0 or 1, u is from 0 to 22;
q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;

r) an alkylethyleneoxy unit of the formula:

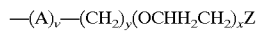

wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;
A is nitrogen or oxygen, M is a water soluble cation, v is 0 or 1, x is from 0 to 100, y is from 0 to 12;
s) substituted siloxy of the formula:

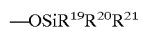

wherein each $R^{19}$, $R^{20}$, and $R^{21}$ is independently
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

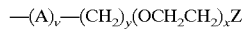

wherein Z is:
a) hydrogen;
b) hydroxyl;
c) —$CO_2H$;
d) —$SO_3^-M^+$;
e) —$OSO_3^-M^+$;
f) $C_1$–$C_6$ alkoxy;
g) substituted aryl, unsubstituted aryl, or mixtures thereof;
h) substituted aryloxy, unsubstituted aryloxy, or mixtures thereof;
i) alkyleneamino; or mixtures thereof;
A is nitrogen or oxygen, M is a water soluble cation, v is 0 or 1, x is from 0 to 100, y is from 0 to 12;
and mixtures thereof, and
B) the balance carriers and adjunct ingredients.

16. A composition according to claim 15 wherein said photosensitizing compound has a positive $\Delta_{triplet}$ yield of at least 10.

17. A composition according to claim 16 wherein said photosensitizing compound has a positive $\Delta_{triplet}$ yield of at least 30.

18. A laundry or cleaning composition comprising:
A) from about 0.1% by weight, of a detersive surfactant, said detersive surfactant is selected from the group consisting of anionic, cationic, nonionic, zwitterionic, ampholytic surfactants, and mixtures thereof;
B) from about 0.001 ppm of a photosensitizing compound having a Q-band maximum absorption wavelength of 660 nanometers or greater having the formula:

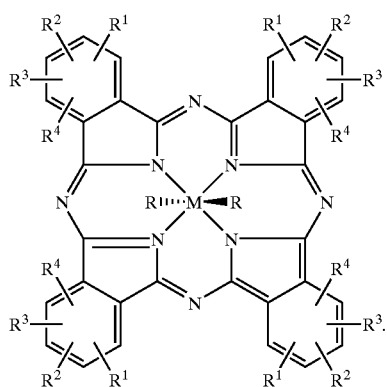

or having the formula:

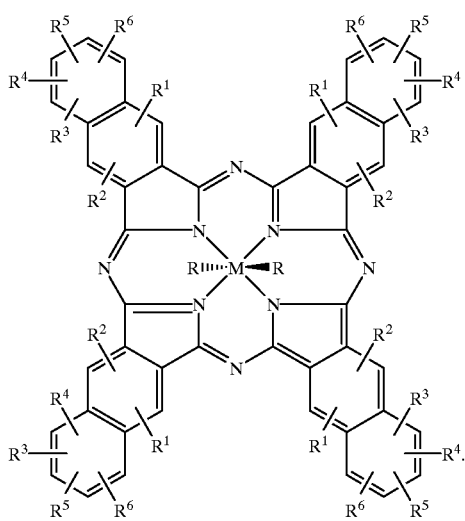

wherein M is a photoactive metal or non-metal selected from the group consisting of Sn, Pt, Pd, Pb, and mixtures thereof;

$R^1$, $R^2$, $R^3$, $R^4$, $R^5$, and $R^6$ units are moieties that provide a positive red shift value of at least 1 when said moieties are substituted for hydrogen;

R units are axial units, said R units independently selected from the group consisting of:

a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;

h) branched alkoxy having the formula:

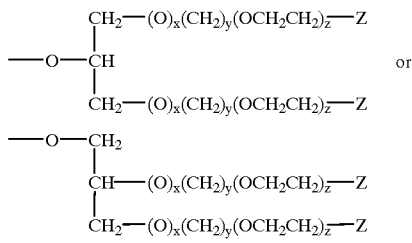

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;

i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) a carboxylate of the formula:

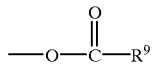

wherein $R^9$ is:

i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
iii) polyhydroxyl substituted $C_3$–$C_{22}$ alkylene;
iv) $C_3$–$C_{22}$ glycol;
v) $C_1$–$C_{22}$ alkoxy;
vi) $C_3$–$C_{22}$ branched alkoxy;
vii) substituted aryl, unsubstituted aryl, or mixtures thereof;
viii) substituted alkylenearyl, unsubstituted alkylenearyl, or mixtures thereof;
ix) substituted aryloxy, unsubstituted aryloxy, or mixtures thereof;
x) substituted oxyalkylenearyl, unsubstituted oxyalkylenearyl, or mixtures thereof;
xi) substituted alkyleneoxyaryl, unsubstituted alkyleneoxyaryl, or mixtures thereof;

p) an alkyleneamino unit of the formula:

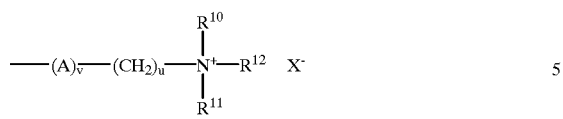

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof; $R^{12}$ is:
i) hydrogen;
ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
A is nitrogen or oxygen; X is chlorine, bromine, iodine, or other water soluble anion, v is 0 or 1, u is from 0 to 22;
q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl $C_3$–$C_{22}$ branched alkenyl, or mixtures thereof;
r) an alkylethyleneoxy unit of the formula:

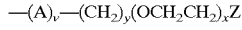

wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;
A is nitrogen or oxygen, M is a water soluble cation, v is 0 or 1, x is from 0 to 100, y is from 0 to 12;

s) substituted siloxy of the formula:

—$OSiR^{19}R^{20}R^{21}$ wherein each $R^{19}$, $R^{20}$, and $R^{21}$ is independently
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

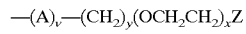

wherein Z is:
a) hydrogen;
b) hydroxyl;
c) —$CO_2H$;
d) —$SO_3^-M^+$;
e) —$OSO_3^-M^+$;
f) $C_1$–$C_6$ alkoxy;
g) substituted aryl, unsubstituted aryl, or mixtures thereof;
h) substituted aryloxy, unsubstituted aryloxy, or mixtures thereof;
i) alkyleneamino; or mixtures thereof;
A is nitrogen or oxygen, M is a water soluble cation, v is 0 or 1, x is from 0 to 100, y is from 0 to 12;
and mixtures thereof; and
B) the balance carriers and adjunct ingredients.

19. A composition according to claim 18 wherein said photosensitizing compound has a positive red shift of at least 10.

20. A composition according to claim 19 wherein said photosensitizing compound has a positive red shift of at least 30.

* * * * *